(12) United States Patent
Wisniewski et al.

(10) Patent No.: US 12,138,623 B2
(45) Date of Patent: Nov. 12, 2024

(54) ADJACENT DUAL BIOLOGICAL NANOPORE READERS

(71) Applicant: ELECTRONIC BIOSCIENCES, INC., San Diego, CA (US)

(72) Inventors: John Andrew Wisniewski, South Salt Lake, UT (US); Vanja Panic, Salt Lake City, UT (US); Eric Mayo Peterson, Salt Lake City, UT (US); Michael Andrew Krupka, San Diego, CA (US); Eric Nathan Ervin, Salt Lake City, UT (US)

(73) Assignee: ELECTRONIC BIOSCIENCES, INC., San Diego, CA (US)

( * ) Notice: Subject to any disclaimer, the term of this patent is extended or adjusted under 35 U.S.C. 154(b) by 777 days.

(21) Appl. No.: 17/332,772

(22) Filed: May 27, 2021

(65) Prior Publication Data

US 2021/0370294 A1 Dec. 2, 2021

Related U.S. Application Data

(60) Provisional application No. 63/031,456, filed on May 28, 2020.

(51) Int. Cl.
*B01L 3/00* (2006.01)
*B82Y 35/00* (2011.01)

(52) U.S. Cl.
CPC . *B01L 3/502715* (2013.01); *B01L 2200/0689* (2013.01); *B01L 2400/0415* (2013.01); *B01L 2400/043* (2013.01); *B82Y 35/00* (2013.01)

(58) Field of Classification Search
CPC ....... B01L 3/502715; B01L 2200/0689; B01L 2400/0415; B01L 2400/043; B82Y 35/00; G01N 33/48721
See application file for complete search history.

(56) References Cited

U.S. PATENT DOCUMENTS

| 5,795,782 | A | 8/1998 | Church et al. |
| 8,968,539 | B2 | 3/2015 | Dunnam et al. |
| 2014/0061048 | A1 | 3/2014 | Turner et al. |
| 2018/0088104 | A1 | 3/2018 | Aksimentiev et al. |
| 2018/0095067 | A1* | 4/2018 | Huff ................. G01N 33/48721 |
| 2020/0306759 | A1* | 10/2020 | Kwon ................ G01N 15/1023 |
| 2021/0299671 | A1* | 9/2021 | Lynn ..................... B01L 3/5082 |

OTHER PUBLICATIONS

Arase et al., "Magnetophoretic Velocity Modulation Mass Analysis of a Single Microparticle in an Atmosphere", Analytical Chemistry, 2006, 78:6660-6663.
Branton et al., "The Potential and Challenges of Nanopore Sequencing", Nature Biotechnology, 2008, 26:1146-1153.
Butler et al., "Single-Molecule DNA Detection with an Engineered MspA Protein Nanopore", Proceedings of the National Academy of Sciences, Dec. 30, 2008, 105(52):20647-20652.

(Continued)

*Primary Examiner* — Jill A Warden
*Assistant Examiner* — John McGuirk
(74) *Attorney, Agent, or Firm* — Gregory P. Einhorn; Greer, Burns & Crain, Ltd.

(57) ABSTRACT

Devices and methods are provided that utilize two adjacent nanopore readers for sequencing of a polymer or a portion thereof.

21 Claims, 11 Drawing Sheets

(56) References Cited

OTHER PUBLICATIONS

Cenev et al., "Manipulating Superparamagnetic Microparticles with an Electromagnetic Needle", Advanced Materials Technologies, 2018, 3(1700177):9 pages.
Clarke et al., "Continuous Base Identification for Single-Molecule Nanopore DNA Sequencing", Nature Nanotechnology, Apr. 2009, 4(4):265-270.
Corey et al., "Strand Invasion by Oligonucleotide-Nuclease Conjugates", Bioconjugate Chemistry, 1995, 6:93-100.
Dani et al., "MspA Porin-Gold Nanoparticle Assemblies: Enhanced Binding through a Controlled Cysteine Mutation", Nano Letters, 2008, 8(4):1229-1236.
De Vries et al., "Micro Magnetic Tweezers for Nanomanipulation Inside Live Cells", Biophysical Journal, Mar. 2005, 88:2137-2144.
Derrington et al., "Nanopore DNA Sequencing with MspA", Proceedings of the National Academy of Sciences, Sep. 14, 2010, 107(37):16060-16065.
Ervin et al., "Creating a Single Sensing Zone within an Alpha-Hemolysin Pore Via Site Directed Mutagenesis", Bionanoscience, Mar. 1, 2014, 4(1):78-84.
Faller et al., "The Structure of a Mycobacterial Outer-Membrane Channel", Science, Feb. 20, 2004, 303:1189-1192.
Ganchev et al., "Strength of Integration of Transmembrane $\alpha$-Helical Peptides in Lipid Bilayers as Determined by Atomic Force Spectroscopy", Biochemistry, 2004, 43:14987-14993.
Ge et al., "Superparamagnetic Magnetite Colloidal Nanocrystal Clusters", Angewandte Chemie International Edition, 2007, 46(23):4342-4345.
Hahn et al., "Magnetophoretic Immunoassay of Allergen-Specific IgE in an Enhanced Magnetic Field Gradient", Analytical Chemistry, 2007, 79:2214-2220.
Heinz et al., "Selective Extraction and Purification of a Mycobacterial Outer Membrane Protein", Analytical Biochemistry, 2000, 285:113-120.
Howorka et al., "A Protein Pore with a Single Polymer Chain Tethered within the Lumen", Journal of the American Chemical Society, Mar. 22, 2000, 122(11):2411-2416.
Howorka et al., "Sequence-Specific Detection of Individual DNA Strands Using Engineered Nanopores", Nature Biotechnology, Jul. 2001, 19:636-639.
Kim et al., "Highly Efficient Antibody Purification with Controlled Orientation of Protein A on Magnetic Nanoparticles", MedChemComm, 2018, 9:108-112.
Lathrop et al., "Monitoring the Escape of DNA from a Nanopore Using an Alternating Current Signal", Journal of the American Chemical Society, 2010, 132(6):1878-1885.
Lee et al., "Site-Specific Labeling of Proteins Using Unnatural Amino Acids", Molecules and Cells, 2019, 42(5):386-396.
Leong et al., "Magnetophoresis of Superparamagnetic Nanoparticles at Low Field Gradient: Hydrodynamic Effect", Soft Matter, 2015, 11(35):6968-6980.
Lim et al., "Magnetophoresis of Nanoparticles", ACS Nano, 2011, 5(1):217-226.
Lim et al., "Rapid Magnetophoretic Separation of Microalgae", Small, 2012, 8(11):1683-1692.
Lyuksyutov et al., "On-Chip Manipulation of Levitated Femtodroplets", Applied Physics Letters, 2004, 85(10):1817-1819.
Manrao et al., "Nucleotide Discrimination with DNA Immobilized in the MspA Nanopore", PLoS One, Oct. 2011, 6(10):e25723:7 pages.
Manrao et al., "Reading DNA at Single-Nucleotide Resolution with a Mutant MspA Nanopore and Phi29 DNA Polymerase", Nature Biotechnology, 2012, 30(4):349-353.
Movileanu et al., "Detecting Protein Analytes That Modulate Transmembrane Movement of a Polymer Chain Within a Single Protein Pore", Nature Biotechnology, Oct. 2000, 18:1091-1095.
Nanocomposix "Magnetite Nanoparticles", Retrieved on Jul. 30, 2021 via : https://nanocomposix.com/pages/magnetite-nanoparticles, 4 pages.

Niederweis et al., "Cloning of the mspA Gene Encoding a Porin from *Mycobacterium smegmatis*", Molecular Microbiology, 1999, 33(5):933-945.
Nivala et al., "Unfoldase-Mediated Protein Translocation Through an $\alpha$-Hemolysin Nanopore", Nature Biotechnology, Mar. 2013, 31(3):247-250.
Noakes et al., "Increasing the Accuracy of Nanopore DNA Sequencing Using a Time-Varying Cross Membrane Voltage", Nature Biotechnology, 2019, 37(6):651-656.
Oesterhelt et al., "Single Molecule Force Spectroscopy by AFM Indicates Helical Structure of Poly (Ethylene-Glycol) in Water", New Journal of Physics, 1999, 1:6.1-6.11.
Oesterhelt et al., "Unfolding Pathways of Individual Bacteriorhodopsins", Science, Apr. 7, 2000, 288:143-146.
Pamme et al., "Continuous Sorting of Magnetic Cells via On-Chip Free-Flow Magnetophoresis", Lab on a Chip, 2006, 6:974-980.
Park et al., "Fabrication of Magnetic Core@Shell Fe Oxide@Au Nanoparticles for Interfacial Bioactivity and Bio-separation", Langmuir, 2007, 23:9050-9056.
Pavlenok et al., "Hetero-Oligomeric MspA Pores in *Mycobacterium smegmatis*", FEMS Microbiology Letters, 2016, 363(7):8 pages.
Pavlenok et al., "MspA Nanopores from Subunit Dimers", PLoS One, Jun. 2012, 7(6):e38726:12 pages.
Peters et al., "Lateral and Rotational Diffusion of Bacteriorhodopsin in Lipid Bilayers: Experimental Test of the Saffman-Delbrück Equations", Proceedings of the National Academy of Sciences, Jul. 1982, 79:4317-4321.
Purnell et al., "Nucleotide Identification and Orientation Discrimination of DNA Homopolymers Immobilized in a Protein Nanopore", Nano Letters, 2008, 8(9):3029-3034.
Restrepo-Perez et al., "SDS-Assisted Protein Transport Through Solid-State Nanopores", Nanoscale, Aug. 17, 2017, 9(32):11685-11693.
Sievers et al., "Quantitative Measurement of the Magnetic Moment of Individual Magnetic Nanoparticles by Magnetic Force Microscopy", Small, 2012, 8(17):2675-2679.
Song et al., "Structure of Staphylococcal Alpha-Hemolysin, a Heptameric Transmembrane Pore", Science, Dec. 13, 1996, 274:1859-1865.
Stoddart et al., "Single-Nucleotide Discrimination in Immobilized DNA Oligonucleotides with a Biological Nanopore", Proceedings of the National Academy of Sciences, May 12, 2009, 106(19):7702-7707.
Storm et al., "Translocation of Double-Strand DNA Through a Silicon Oxide Nanopore", Physical Review, 2005, E71(051903):10 pages.
Thompson et al., "Rapid Assembly of a Multimeric Membrane Protein Pore", Biophysical Journal, Dec. 2011, 101:2679-2683.
Vercoutere et al., "Discrimination Among Individual Watson—Crick Base Pairs at the Termini of Single DNA Hairpin Molecules", Nucleic Acids Research, 2003, 31(4):1311-1318.
Walker et al., "Key Residues for Membrane Binding, Oligomerization, and Pore Forming Activity of Staphylococcal $\alpha$-Hemolysin Identified by Cysteine Scanning Mutagenesis and Targeted Chemical Modification", Journal of Biological Chemistry, Sep. 29, 1995, 270(39):23065-23071.
Walker et al., "Restoration of Pore-Forming Activity in Staphylococcal Alpha-Hemolysin by Targeted Covalent Modification", Protein Engineering, May 1995, 8(5):491-495.
Worden et al., "Monofunctional Group-Modified Gold Nanoparticles from Solid Phase Synthesis Approach: Solid Support and Experimental Condition Effect", Chemistry of Materials, 2004, 16:3746-3755.
Cadinu et al., "Double Barrel Nanopores as a New Tool for Controlling Single-Molecule Transport" Nano Letter, 2018, v 18, p. 2738-2745.
International Search Report and Written Opinion dated Aug. 20, 2021 in PCT Patent Application No. PCT/US2021/034597, filed on May 27, 2021, 17 pages.
Liu et al., "Flossing DNA in a Dual Nanopore Device", Small, Dec. 20, 2019, 11 pages.
Pud et al., "Mechanical Trapping of DNA in a Double-Nanopore System", Nano Letters, Dec. 1, 2016, 30 pages.

(56) References Cited

OTHER PUBLICATIONS

Yuan et al., "Controlling DNA Translocation Through Solid-state Nanopores", Nanoscale Research Letters, Apr. 15, 2020, 15(80):9 pages.
Zhang et al., "Single Molecule DNA Resensing Using a Two-Pore Device", Small, Oct. 17, 2018, 11 pages.

\* cited by examiner

FIG. 6A
FIG. 6B
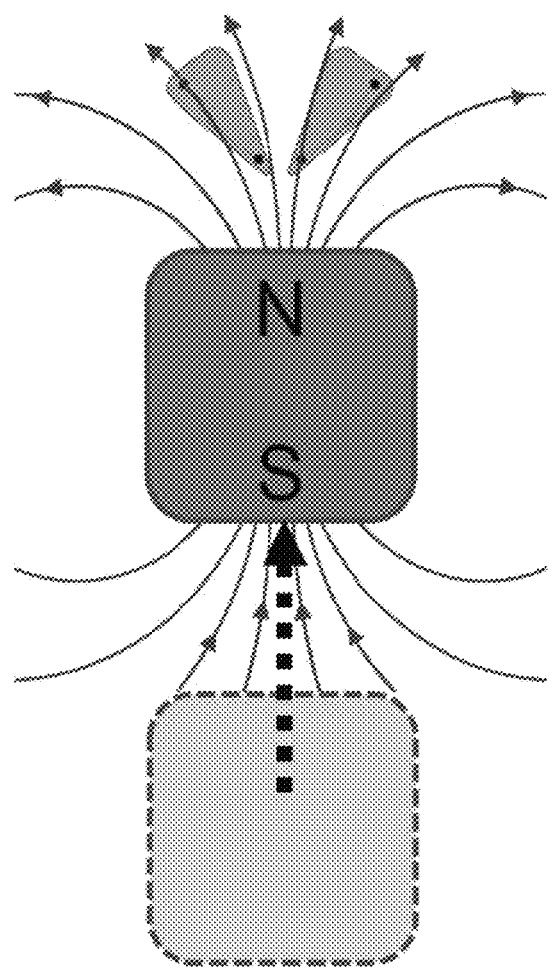
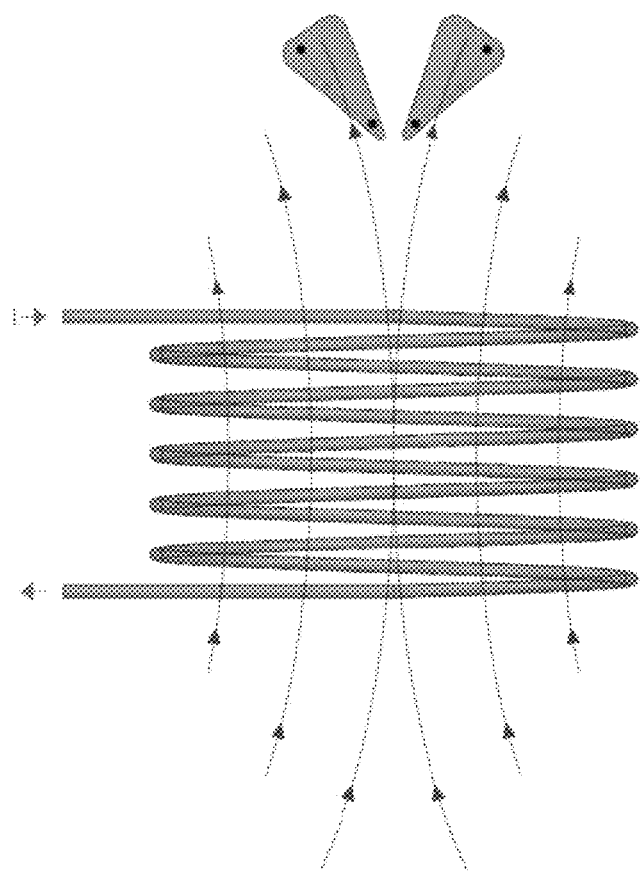

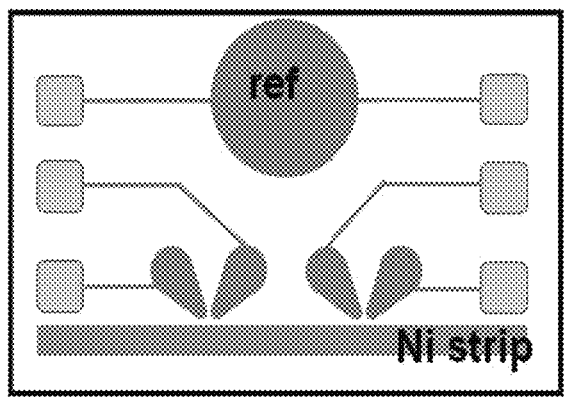
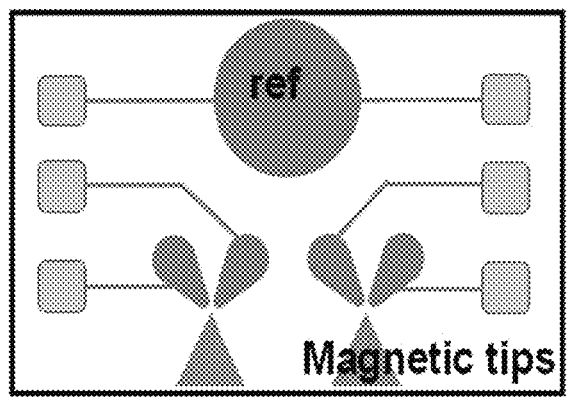
FIG. 8A
FIG. 8B
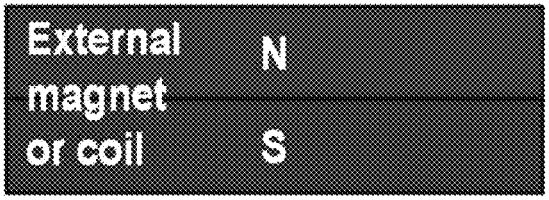
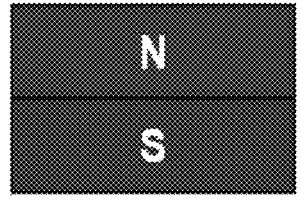

FIG. 9A
Microwells in SU-8 layer
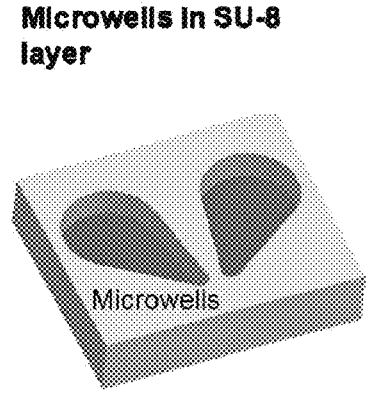
FIG. 9B
Form planar lipid bilayers in both wells
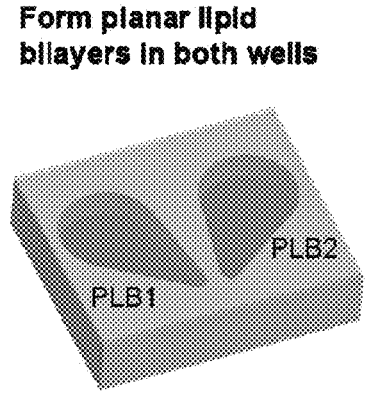
FIG. 9C
Insert magnetic particle- tagged αHL into PLB 1
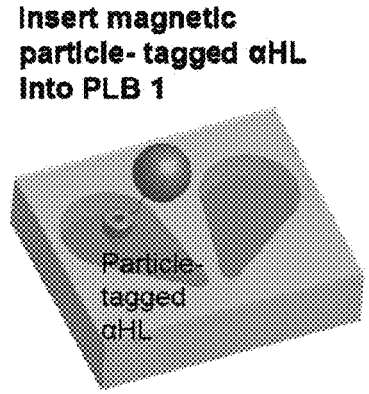
Insert magnetic particle- tagged MspA into PLB 2
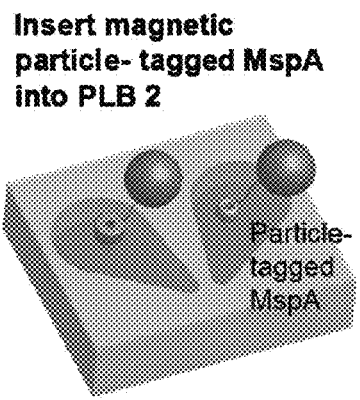
Apply magnetic field to bring tagged readers into capture zone
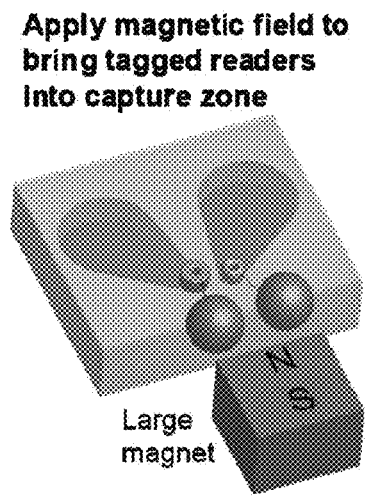
FIG. 9D
FIG. 9E

FIG. 10A        FIG. 10B        FIG. 10C
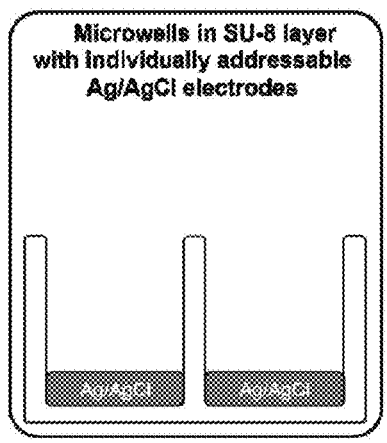 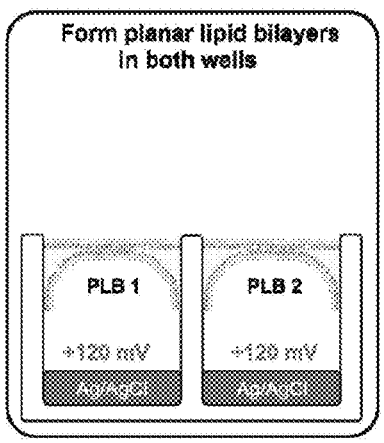 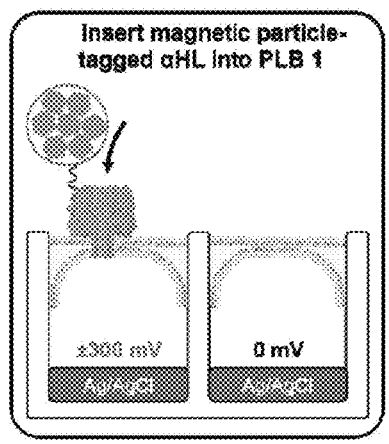
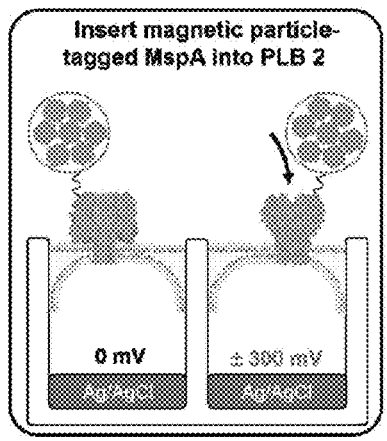 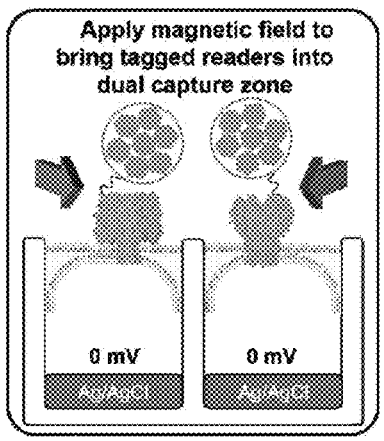
FIG. 10D        FIG. 10E FIG. 11A
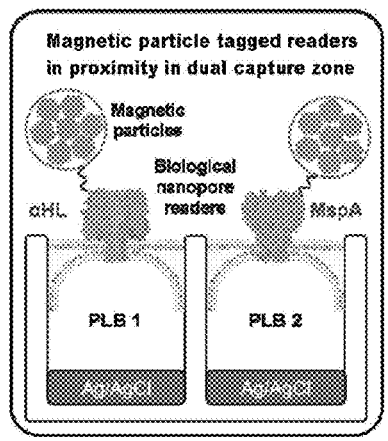
FIG. 11B
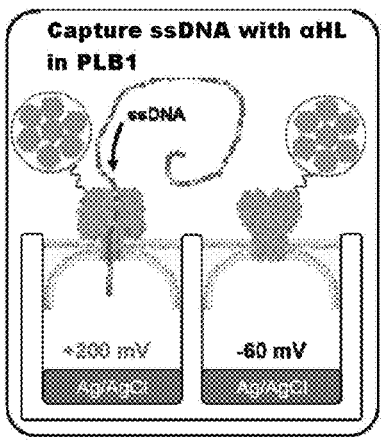
FIG. 11C
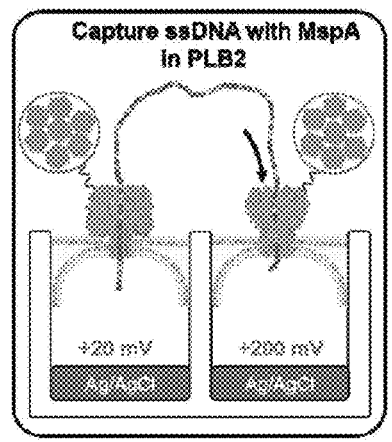
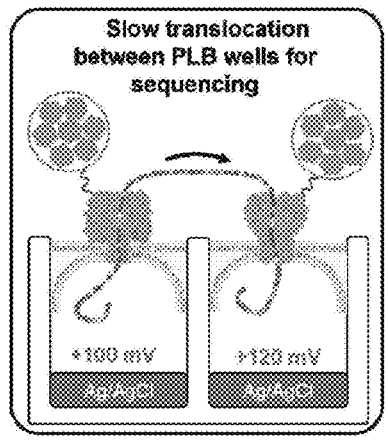
FIG. 11D
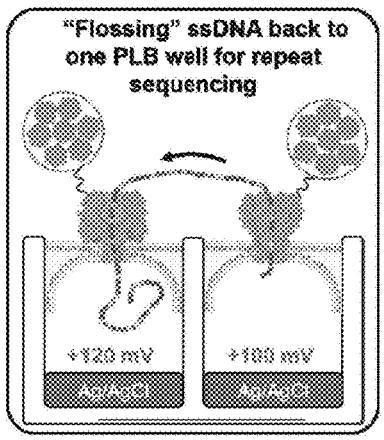
FIG. 11E

ADJACENT DUAL BIOLOGICAL NANOPORE READERS

RELATED PATENT APPLICATION

This patent application claims the benefit of U.S. provisional patent application No. 63/031,456, filed on May 28, 2020, entitled ADJACENT DUAL BIOLOGICAL NANOPORE READERS, naming John Andrew Wisniewski et al. as inventors. The entire content of the foregoing patent application is incorporated herein by reference for all purposes, including all text, tables and drawings.

FIELD

The technology relates in part to nanopore devices and their use for sequencing nucleic acids and proteins.

BACKGROUND

In 1995, Church et al. first proposed the idea of polymer sequencing using a nanopore (U.S. Pat. No. 57/957,820). Since then, nanopores (both synthetic and biological) have been extensively studied for their ability to directly sequence DNA, and to a lesser extent RNA. At this point in time, it could be argued that nanopore-based sequencing is the future of genomics, transcriptomics, epigenomics, and epitranscriptomics due to the currently associated (and further anticipated) capabilities. These include but are not limited to direct single-molecule analysis and the associated ability to profile a given sample, long read lengths, high speed/throughput, lower cost, improved ease-of-use, increased accessibility, and better system/analysis logistics, relative to present, standard sequencing-by-synthesis (SBS) technologies.

SUMMARY

Provided herein in certain aspects are methods for nanopore-based sequencing, and devices and methods of making devices for nanopore-based sequencing applications.

Provided herein, in certain aspects is a device comprising a chip comprising two adjacent wells separated by a distance, each of the wells comprising an opening aperture, a bottom and an electrode disposed at the bottom.

Also provided in certain aspects is a device comprising a chip comprising two adjacent wells separated by a distance, each of the wells comprising an opening aperture, a bottom and an electrode disposed at the bottom. A separate seal over the opening aperture of each of the wells. A nanopore reader in each seal, wherein each reader independently is tethered to one or more magnetic particles. A first component configured to apply a magnetic field across the wells. A second component configured to detect an interaction between each reader and a molecule that can be introduced to the device and contacted by the reader.

Also provided in certain aspects is a device comprising a nanopore reader tethered to one or more nanoparticles.

Also provided in certain aspects is a device comprising a nanopore reader tethered to one or more magnetic particles.

Also provided in certain aspects is a nanopore reader tethered to one or more magnetic particles.

Also provided in certain aspects is a chip comprising dual wells.

Also provided in certain aspects is a method for determining a polymer sequence. Contacting a fluid containing a polymer comprising monomeric units, a first end and a second end, with a device comprising a chip, a first well disposed adjacent to a second well on the chip, a first seal over the first well and a second seal over the second well, and a first reader in the first seal and a second reader in the second seal, wherein the first reader and the second reader each is a transmembrane channel polymer reader. Electrophoretically and/or electroosmotically driving the first end of the polymer from the fluid through the first reader into the first well; thereby capturing the first end of the polymer by the first reader. Electrophoretically and/or electroosmotically driving the second end of the polymer in the fluid through the second reader into the second well; thereby capturing the second end of the polymer by the second reader. Electrophoretically driving at least a portion of the polymer through the first reader into the first well or through the second reader into the second well. Identifying monomeric units of the polymer based on a current signature of each of the monomeric units, translocation time and/or associated current noise level modulation as the polymer translocates through the first reader or the second reader, thereby determining the sequence of the polymer.

Also provided in certain aspects is a method for determining a polymer sequence or portion thereof. Contacting a fluid containing a polymer comprising monomeric units, a first end and a second end, where the polymer is a protein or a peptide, with a device comprising a chip, a first well disposed adjacent to a second well on the chip, a first seal over the first well and a second seal over the second well, and a first reader in the first seal and a second reader in the second seal, wherein the first reader and the second reader each is a nanopore reader. Electrophoretically and/or electroosmotically driving the first end of the polymer from the fluid through the first reader into the first well; thereby capturing the first end of the polymer by the first reader. Electrophoretically and/or electroosmotically driving the second end of the polymer in the fluid through the second reader into the second well; thereby capturing the second end of the polymer by the second reader. Electrophoretically driving at least a portion of the polymer through the first reader into the first well or through the second reader into the second well. Identifying monomeric units of the polymer based on a current signature of each of the monomeric units, translocation time and/or associated current noise level modulation as the polymer translocates through the first reader or the second reader, thereby determining the sequence of the polymer or a portion thereof.

Also provided in certain aspects is a method for sequencing a polymer. Providing adjacent nanopore readers. Contacting the adjacent nanopore readers with a polymer. Capturing the polymer with the adjacent nanopore readers. Controlling the voltage bias applied between the two nanopore readers to floss the polymer between the two readers and to allow multipass sequencing.

Also provided in certain aspects is a method for sequencing using dual biological nanopore readers. Providing two adjacent biological nanopore readers tagged with magnetic particles. Positioning the magnetic particle-tagged readers into proximity by an external magnetic field. Capturing one end of a polymer by the first nanopore reader by providing high positive voltage bias to the first nanopore reader. Reducing the voltage bias on the first nanopore reader and capturing the other end of the polymer by the second nanopore reader by providing high positive voltage bias to the second nanopore reader. Applying a small voltage bias between the first nanopore reader and the second nanopore reader to initiate dual pore sequencing. Reversing the voltage bias between the first nanopore reader and the second nanopore reader to initiate reverse translocation and sequencing.

Also provided in certain aspects is a method of sequencing. Providing two adjacent biological nanopore readers. Contacting a polymer comprising monomeric units with the two adjacent biological nanopore readers. Identifying monomeric units of the polymer as the polymer translocates through one or both adjacent biological nanopore readers.

Also provided in certain aspects is a method of sequencing utilizing a sequencing chip and a magnetic field.

Also provided in certain aspects is a method of attaching a magnetic particle to a nanopore reader. Providing a nanopore reader. Modifying a residue of the nanopore reader that is on the cis side of the reader when the reader is inserted into a seal to comprise an attachment site. Providing a bifunctional polymer linker having a first end and a second end, wherein a magnetic particle is attached to the first end of the polymer linker. Conjugating the second end of the polymer linker to the attachment site on the cis side of the nanopore reader.

Also provided in certain aspects is a method for insertion of magnetic particle tagged nanopore readers into PLBs and migration of the magnetic particle tagged nanopore readers into a dual capture zone. Providing a first and a second well with electrodes in each well, wherein the first well and the second well are on the same platform. Forming a first planar supported lipid bilayer over the first well and a second planar supported lipid bilayer over the second well. Applying high voltage bias to allow insertion of a particle-tagged nanopore reader into the first planar supported lipid bilayer. Applying high voltage bias to allow insertion of a particle-tagged nanopore reader into the second planar supported lipid bilayer. Generating a high magnetic field gradient to move magnetic particle-tagged readers in the first planar supported lipid bilayer and the second planar supported lipid bilayer to a dual-capture zone.

Certain implementations are described further in the following description, examples and claims, and in the drawings.

BRIEF DESCRIPTION OF THE DRAWINGS

The drawings illustrate certain implementations of the technology and are not limiting. For clarity and ease of illustration, the drawings are not made to scale and, in some instances, various aspects may be shown exaggerated or enlarged to facilitate an understanding of particular implementations.

FIG. 1A illustrates magnetic control of biological nanopore readers using an external magnetic field which induces migration of magnetic nanoparticles tethered to biological nanopore readers, positioning them close together in the confinement region of the bilayer membrane. FIG. 1B illustrates dual biological nanopore sequencing: closely spaced biological nanopore readers capture single-stranded DNA simultaneously, allowing the ssDNA to be "flossed" between the two readers to control the translocation velocity and allow multipassing by controlling the voltage bias applied between the two microwells (also referred to as wells).

FIG. 2A shows magnetic particles migrating up the magnetic field gradient (left) into the confinement region. FIG. 2B shows the forces acting on a magnetic nanoparticle tethered to a protein nanopore in a lipid membrane that determine the terminal velocity, $v_t$: nanopore-bilayer viscous drag, $F_{d,pore}$, particle-solution viscous drag, $F_{d,part}$, and magnetophoretic force, $F_{mag}$.

FIG. 3C shows the area-normalized probability of locating a magnetic nanoparticle beyond a given position along the magnetic field gradient.

FIG. 5A illustrates a chip layout. FIG. 5B shows an adjacent snowcone shaped PLB well configuration. All wells are in a 3-20 μm deep SU-8 layer with the bottom of the well backfilled with Ag/AgCl. FIG. 5C shows an adjacent snow-cone shaped PLB well configuration, depicting major length, major width, minor width, and angle (theta) between the virtual major length axis of each well.

FIGS. 6A and 6B show magnet orientation in the chip reader. FIG. 6A shows a permanent rare earth magnet that translates into position in plane near the dual PLBs. FIG. 6B shows current applied to an electromagnetic coil in a fixed position near the PLBs to induce a magnetic field.

FIG. 7A shows magnetic flux density around 125 mil magnet oriented with magnetic poles in the x-axis. FIG. 7B shows line scans of magnetic flux density in the x-direction along center of the chip at a point 0.5 mm above the surface of the magnet, corresponding to the thickness of the chip. FIG. 7C shows magnetic flux gradient x-scan showing peaks near the edge of the magnet.

FIGS. 8A and 8B illustrate magnetic nanostructures built into the dual nanowell reader chip. FIG. 8A shows a magnetic strip composed of Ni or other metals with high magnetic susceptibility with thickness and depth of 1-50 μm spans multiple PLB pairs and generates strong local magnetic field gradient induced by an external permanent or electromagnet. FIG. 8B shows magnetic tip structures composed of similar materials positioned near the constriction point of each PLB pair.

FIGS. 9A-E diagram the insertion of magnetic particle tagged readers into PLBs and migration into the dual capture zone. FIG. 9A shows microwells photopatterned into SU-8 photoresist with Ag/AgCl electrodes in each well. FIG. 9B shows formation of planar supported lipid bilayer over each well using a magnetic stir bar or lipid painting method. FIG. 9C shows capture of particle-tagged αHL into PLB1. FIG. 9D shows capture of particle-tagged MspA into PLB2. FIG. 9E shows a magnet moved into position to generate high magnetic field gradient to move magnetic particle-tagged readers into dual-capture zone of PLBs.

FIGS. 10A-E illustrate a protocol for construction of a dual biological nanopore reader device. FIG. 10A shows microwells photopatterned into SU-8 photoresist with Ag/AgCl electrodes in each well. FIG. 10B shows formation of planar supported lipid bilayer over each well using a magnetic stir bar or lipid painting method. FIG. 10C shows application of high voltage bias (100-300 mV) to allow insertion of particle-tagged αHL into PLB1. FIG. 10D shows application of voltage bias for insertion of particle-tagged MspA into PLB2. FIG. 10E shows a magnet moved into position to generate high magnetic field gradient to move magnetic particle-tagged readers into dual-capture zone of PLBs.

FIGS. 11A-E illustrate a protocol for ssDNA capture for dual biological nanopore sequencing. FIG. 11A shows magnetic particle-tagged readers in proximity in dual capture zone. FIG. 11B shows ssDNA captured by PLB1 reader (e.g., αH) using high positive voltage bias. FIG. 11C shows voltage bias on PLB1 reader reduced to slow translocation, and high bias applied to PLB2 reader (e.g., MspA) to capture free end of ssDNA. FIG. 11D shows application of voltage bias with small difference between PLBs 1 and 2 to initiate slow translocation between readers for dual pore sequencing. FIG. 11E shows voltage bias between PLBs reversed to initiate reverse translocation and sequencing; this step is repeated to sequence ssDNA multiple times.

DETAILED DESCRIPTION

Figure 1A:
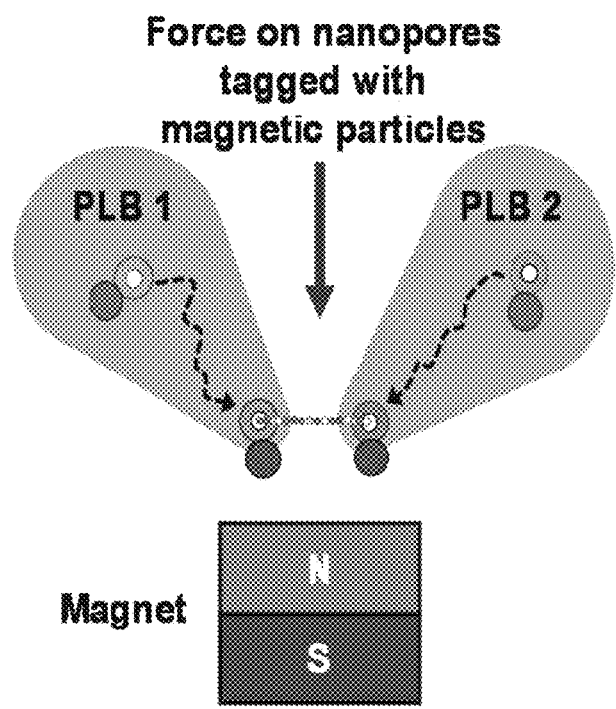
FIGS. 1A and 1B provide an example of adjacent dual nanopore readers and use thereof.
Figure 1B:
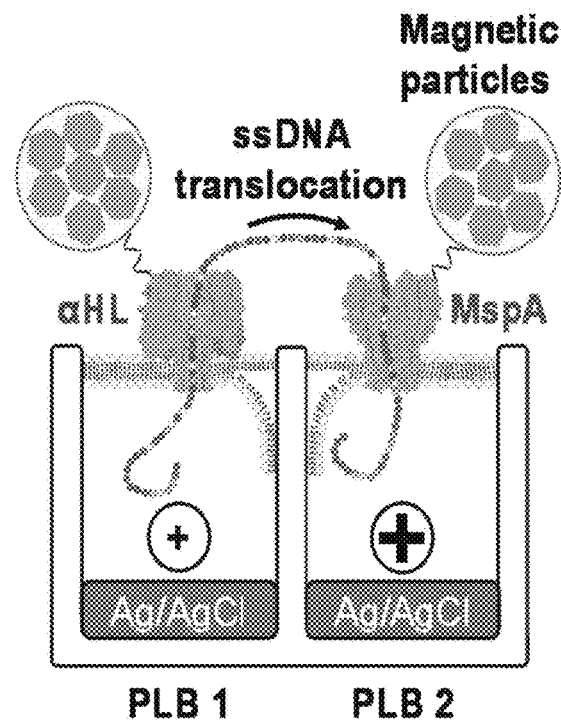

The technology relates in part to a system that includes two biological nanopore readers magnetically positioned in individual planar lipid bilayers (PLBs) in close proximity (e.g., about 10 nm to about 5 micrometers) to one another, each with its own high speed field-programmable gate array (FPGA) controlled voltage biasing (e.g., see FIGS. 1A and 1B). A system described herein in part can be utilized for (1) controllably capturing a target polymer across the two readers; (2) ensuring that the polymer is elongated/stretched through each reader (a requirement for nanopore-based strand sequencing); (3) controlling the rate and direction of strand translocation through the readers using voltage bias without the use of an enzyme/motor; (4) flossing/multipassing the polymer back and forth through the readers in order to re-read and improve sequencing accuracy; and (5) using two different readers simultaneously but independently for cross-validation, further improving the sequencing accuracy. Such system and methods have nanopore-based polymer sequencing applications, including, but not limited to, sequencing single-stranded DNA and RNA, double-stranded DNA and RNA, proteins and peptides.

The adjacent-dual-biological-nanopore-based sequencing platform described herein can combine the translocation control provided by dual-pore readers with the sequence sensitivity of biological nanopores to enable high-accuracy (>99.9%) sequencing. For example, systems described herein address the speed of polymer (e.g., nucleic acid) translocation which compromises accurately resolve individual monomers (e.g., nucleotides) and the noise associated with strand compression and relaxation during free translocation that prohibits accurate reading of individual monomers (e.g., nucleotides) based on the uncertain position of the strand at any given moment. The systems and methods described herein that avoid the limitations of enzymes/motors. Consequently, and significantly advantageous, systems described herein allow simplistic library preparation procedures that do not introduce artifacts/biases.

Without being limited by theory, the dual-pore system described herein induces a counter balance mechanism to control the rate of translocation through the readers. Here, one nanopore reader with its electrode and high-speed biasing mechanism functions as the "motor/brakes" or translocation control by pulling the polymer against the other nanopore reader and its electrode and high-speed biasing mechanism. The net translocation direction and speed are controlled via the ability to independently bias across each reader and have a net translocation force on the polymer through one of the readers, pulling against the other reader.

The innovations behind the platform and methodology are numerous, including (1) the utilization of two adjacent chip-based PLBs whose width narrows as their proximity to one another also decreases; (2) the use of a magnetic field across those PLBs to pull individual nanopore readers tagged with magnetic particles into close proximity of one other; (3) the utilization of voltage induced protein/PLB incorporation to insert one reader type into one PLB and another reader type into an adjacent PLB on the same chip/platform; and (4) the utilization FPGA logic in combination with high-speed DC voltage bias switching to semi-automate the capture of target polymer into the two adjacent biological readers and control the direction and rate of translocation, including the ability to floss/multipass the polymer back and forth through the readers in order to re-read the sequence or portion of the sequence of the polymer.

Magnetophoretic Migration of Nanopores Tagged with Magnetic Nanoparticles

In order to bring the two biological nanopore readers (e.g., α-hemolysin and MspA) within a few hundred nanometers from each other within separate but adjacent PLBs, in some embodiments of the described adjacent-dual-biological-nanopore-based sequencing platform, each biological nanopore reader can be tagged with a single magnetic nanoparticle. The biological nanopore readers then can be guided in the lipid bilayers to their appropriate measurement position using an external magnetic field. Magnetic nanoparticles are widely used for biomolecule separations, where permanent magnets can induce rapid migration of magnetic nanoparticles over long distances (mm-cm). One of the most common are magnetite ($Fe_3O_4$) nanoparticles, which are available from multiple vendors with a variety of surface functionalizations. Although bulk magnetite is ferrimagnetic and can adopt a permanent magnetic moment, the magnetic moment of nanocrystalline magnetite realigns randomly due to random thermal fluctuations. However, these nanoparticles are superparamagnetic, and they adopt strong magnetic moments when placed in an external magnetic field. Under magnetic fields greater than 0.5 T magnetite nanoparticles reach a maximum saturation magnetization of 50-90 $Am^2\ kg^{-1}$.

Figure 2A:
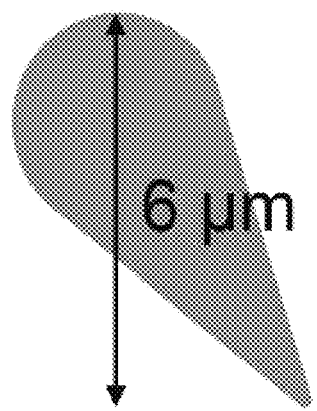
FIGS. 2A and 2B provide a diagram of microwell PLB.
Figure 2B:
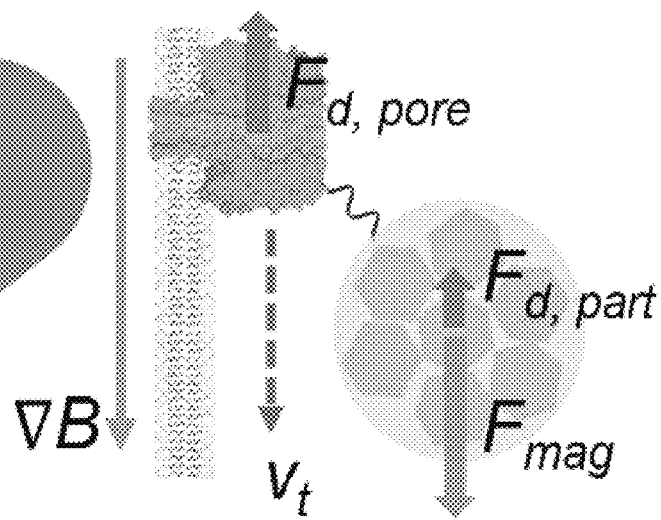

This induced magnetic dipole moment is subject to a force in a magnetic field gradient proportional to the saturation magnetization of the dipole, $M_s$, the mass of the particle, m, and the magnetic field, B, gradient: $F_{mag}=(M_s m\nabla)B$. Since the magnitude of the magnetic dipole moment is proportional to the mass of the particle, larger particles experience stronger forces. For spherical magnetic nanoparticles in solution, the field gradient force induces migration of the particles, known as magnetophoresis. The force driving migration, shown in FIG. 2B, is proportional to the particle density, ρ (5.2 g $cm^{-3}$ for magnetite), and the cube of the diameter, d:

$$F_{mag}=(M_s \rho \pi/6 d^3 \nabla)B \qquad \text{Eq. 1}$$

High magnetic fields (>0.5 T) and magnetic field gradients are needed to induce migration of magnetic particles. Simple permanent magnets in contact with sample vials can generate field gradients that vary from 10-100 $Tm^{-1}$, which are sufficient to concentrate large magnetic nanoparticles used for biomolecule separations. Stronger magnetic field gradients are needed to induce migration of smaller particles, which can be produced with magnets incorporated into thin cells that generate gradients up to $10^3$ T m$^{-1}$. Magnetic microstructures, such as magnetic tips and magnetic tweezers, in an external magnetic field can produce even higher local gradients in the $10^3$ to $10^4$ T m$^{-1}$ range. In some embodiments, the component configured to apply a magnetic field across the wells and induce migration of magnetic particles is an external magnet alone (e.g., a rare-earth permanent magnet) or electromagnet coil. In other embodiments, the component configured to apply a magnetic field across the wells is an external magnet (e.g., a permanent magnet or an electromagnet coil) with magnetic microstructures made of ferromagnetic, paramagnetic, or super paramagnetic materials with high relative permeabilities (e.g., Ni, magnetite) near the microwells, which include but are not limited to magnet tips, magnetic tweezers, coils, or strips. In other embodiments, the component is a magnetic probe consisting of a permanent magnet or electromagnet coil built into a sharp micro-scale probe that can be moved near the wells to apply a magnetic field.

Assuming a magnetic field in excess of 0.5 T and a gradient of $10^3$ Tm$^{-1}$, a 50 nm diameter ferrite nanoparticle would experience a magnetic migration force of ~25 fN. When the particle begins to migrate, the magnetophoretic force is countered by viscous drag, Fd, on the particle, which can be estimated using Stoke's law:

$$F_d = -3\pi\eta dv \quad \text{Eq. 2}$$

Where q is the viscosity, and v is the migration velocity of the particle. Since the drag force increases linearly with the velocity, eventually the viscous drag will counteract the magnetophoretic forces and the particle will achieve terminal velocity, shown in FIG. 2B. Equations 1 and 2 can be used to solve for the terminal velocity of a particle, $v_t$, when $F_{mag} = -F_d$:

$$v_t = (2M_s \rho r^2 \cdot \nabla) B/9\eta \quad \text{Eq. 3}$$

Under the influence of the magnetic field gradient described above, a 50 nm diameter particle would reach a terminal velocity of 50 µm s$^{-1}$, allowing it to traverse a 3 µm pore in 120 ms.

However, a protein nanopore also experiences drag due to the high viscosity of phospholipid membranes (0.1 Pa s) compared to water (0.001 Pa s), which slows the magnetophoretic migration. A pore-forming protein, e.g. alpha hemolysin, with a radius of ~10 nm migrating in a lipid bilayer would experience 7-fold higher drag forces than the 50 nm magnetic particle in aqueous solution, reduces the migration velocity to 7 µm s$^{-1}$. Even with the combined drag, the nanopore can still traverse the membrane in less than a second, allowing rapid focusing of the nanopores into the constriction region.

Although strong enough to induce migration, the magnetic forces cannot pull the protein nanopores out of the lipid membrane. The force required to remove hydrophobic peptides and proteins from phospholipid bilayers has been extensively studied with atomic force microscopy. These forces, in the 30-200 pN range, are 3 orders of magnitude larger than the magnetic force on the nanoparticles, indicating that the nanoparticle manipulation will not induce desorption of proteins from the bilayer.

Figure 3A:
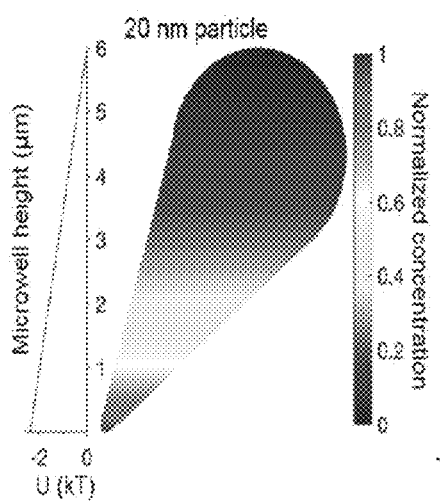
FIGS. 3A-C illustrate concentration profiles of magnetic particles-tethered protein nanopores in a magnetic field gradient. Potential energy profiles and normalized concentration profiles calculated from Equation 4 for 20 nm (FIG. 3A) and 50 nm (FIG. 3B) diameter particles.
Figure 3B:
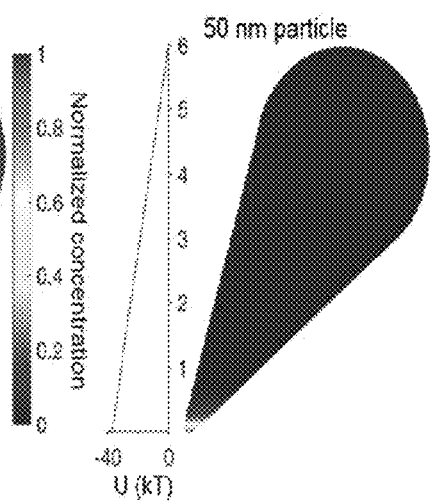

These magnetic forces must also overcome random thermal diffusion to confine the nanopores to the constriction region of the well. The magnitude of concentrating effect of the magnetic forces can be modeled using a Boltzmann distribution based on the ratio of the magnetic potential energy along the membrane to the thermal energy. A diagram of a 6 µm long membrane-spanning well with the magnetic field gradient oriented in the y-axis is shown in FIGS. 3A and 3B. The spatial distribution of nanopore excess concentration, C, in the membrane well can be determined from the magnetic potential energy distribution, $U_{mag}(x,y)$:

$$C(x,y) = e^{U_{mag}(x,y)/kT} \quad \text{Eq. 4}$$

Figure 3C:
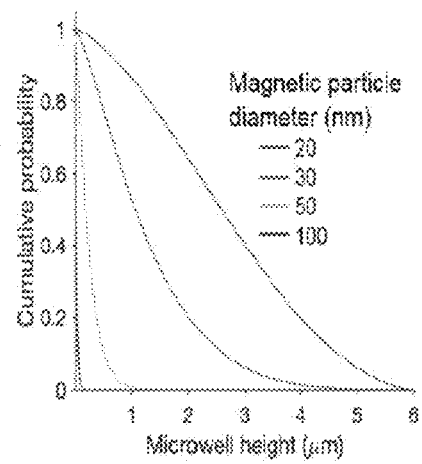

The magnetic field gradient is constant and aligned with the vertical axis, y, and there is no gradient in the horizontal axis, x. The potential energy distribution is the magnetic force multiplied by the distance, I, from the distal end of the membrane: $U_{mag}(x,y) = -F_{mag}(I-y)$. The excess concentration profile are shown in FIGS. 3A and 3B for 30 and 50 nm magnetic nanoparticles in a magnetic field gradient of 1000 T m$^{-1}$. These profiles show a high concentration of particles near the constriction region, and that the trapping energetics increase with the particle volume. However, the area of the membrane decreases as the membrane tapers to the constriction zone, which increases the energy needed to concentrate the nanopores. FIG. 3C shows a probability distribution for locating nanopores (scaled by area) along the magnetic field gradient. Based on this model, nanopores tethered to 100 nm particles are confined to a 90 nm region in the constriction zone with 99% certainty. The confinement region, and thus the average spacing between the two protein nanopores, can be tuned by changing the magnetic field gradient, and/or the size of the magnetic nanoparticles.

Figure 4:
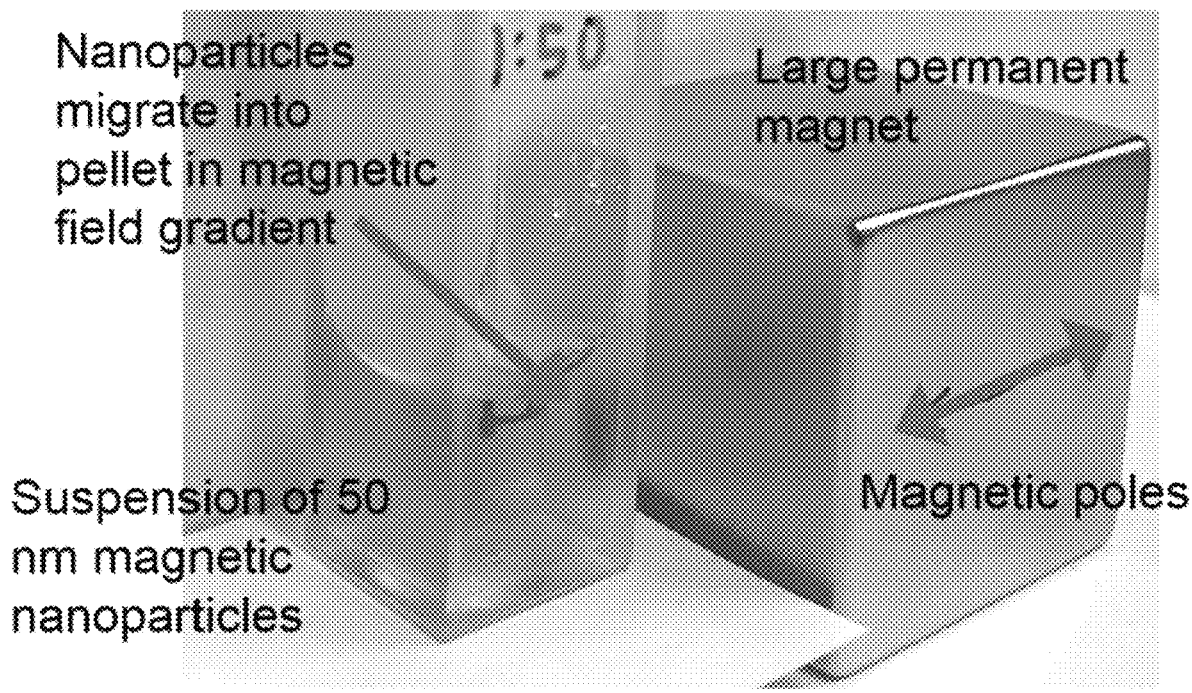
FIG. 4 shows migration of 50 nm magnetic particles in viscous solution (solution in cuvette) in a magnetic field gradient induced by a 25 mm cube permanent magnet (right side of image). The magnetic poles are oriented as shown by the arrow in the image. Magnetic nanoparticles have migrated in the magnetic field gradient to form a concentrated pellet at the wall of the cuvette, seen as a dark ellipsoid shape on the right side of the cuvette.

Experiments have demonstrated that simple permanent magnets are capable of inducing migration of magnetic nanoparticles in viscous media. In mixtures of glycerol and water with a viscosity chosen to simulate the drag of a magnetic nanoparticle-tethered biological nanopore reader, small 50 nm magnetic particles can be induced to migrate and concentrated into a confined region near a rare-earth permanent magnet (FIG. 4). This result indicates that magnetophoresis can be used to move and confine magnetic particles in conditions similar to those in the dual PLB microwells.

Readers

The biological nanopore reader utilized to sequence a single-stranded polymer (DNA or RNA), double-stranded polymer (DNA or RNA), protein or peptide can be any biological nanopore, ion channel, transmembrane protein or DNA nanopore suitable for strand sequencing applications, and be either the wild type form of that nanopore, ion channel, or transmembrane protein or a mutated, engineered, and/or chemically modified form. In some embodiments, the sensing zone of a nanopore reader (e.g., αHL or MspA) can be mutated to both improve DNA translocation and have a single, sharp sensing zone that could resolve/sequence individual nucleotides. Using DNA strand trapping methods allowed various groups to relatively quickly perform this work, optimizing various nanopore readers, including αHL, MspA, and CsG. In certain embodiments, mutations could also target the overall charge, size, and three-dimensional shape of the nanopore, or could be made to alter the interaction with the membrane (i.e., to more/less easily insert into a membrane, to remain inserted in the membrane longer). In certain embodiments, more aggressive truncation or insertion of several amino acids could remove or introduce a recognition site, enhance sensitivity, and impart selectivity of a desired analyte. In some embodiments, mutations could also involve the introduction of non-natural amino acids with unique side chains and functional properties. In some embodiments, oligomeric proteins could be synthesized as a single chain. For instance, a hemolysin, a heptamer, could have its seven subunits expressed as a single protein, with amino acid linkers introduced in between what were formerly separate subunits to connect them into a single chain that will fold into a functional nanopore. In certain embodiments, various tags can be added either through in vitro conjugation to the desired pore site or through fusion protein expression to enhance the nanopore performance.

In certain embodiments, completely synthetic biological based nanopores or ion channels would also be suitable. Non-specific, non-inclusive examples of biological nanopore, ion channels, or transmembrane proteins which could be utilized include but are not limited to alpha-hemolysin (αHL), aerolysin, *Mycobacterium smegmatis* porin A (MspA), *Escherichia coli* CsgG, Cytolysin A (ClyA), and outer membrane protein F (OmpF). Non-inclusive examples of synthetic engineered biological nanopores include DNA nanopores (also referred to as "DNA-based nanopores" or "DNA origami nanopores") and engineered peptide nanopores. In certain embodiments, chemical crosslinking agents that covalently link the individual subunits or that tune the performance of the nanopore readers could be made.

Tagging Protein Pore Readers with Magnetic Nanoparticles

In some embodiments, to induce migration in an external magnetic field, the biological nanopore readers can be tagged with a single magnetic nanoparticle via a polymer linker. In certain embodiments, each reader can be engineered such that it contains a single attachment adapter for binding the above described magnetic nanoparticles. In some embodiments, adapters can be added to engineered residues positioned on the cis side of the reader, and then can be conjugated with a compatible reactive or high-affinity binding group on a linker polymer. The opposite end of the linker polymer can contain an orthogonal reactive or affinity binding group for attachment to chemically modified magnetic nanoparticles. In some embodiments, the orthogonal pair allowing for attachment to the magnetic nanoparticles could include (but is not limited to) biotin/streptavidin, epitope tags (e.g. c-Myc or HA tags), 6-His/NiNTA, alkyne/azide, transcyclooctene/tetrazene, Snaptag/$O^6$-benzylguanine or gold binding peptide/gold surface coating on magnetic nanoparticles. A process for non-limiting examples of biological nanopore readers, αHL and MspA, are described herein.

A first biological nanopore reader, alpha-hemolysin (αHL) is composed of seven monomer units that fold to form the heptameric protein pore. Wild type αHL does not have any naturally occurring cysteine residues and its N- and C-termini are located on the cis-side of the pore so they both can be used to readily attach a flexible linker. Various residues in this region can be mutated to cysteine that can serve as an attachment point for maleimide-biotin or other bifunctional linkers to allow tethering to magnetic nanoparticles. In addition to a single cysteine mutant, an alternative strategy would be to link the adapter to surface exposed amino groups, either from lysine or the N-terminal amine. In this scenario, an NHS-ester would be used as the reactive group specific to the protein nanopore reader on the bifunctional linker.

In some embodiments, to ensure that only a single linker is present per protein reader, only one of seven monomers may be selected for containing the reactive cysteine group. To facilitate the separation of heteroheptameric pores with a single linker, the αHL mutant subunit can be equipped with a polyaspartate (D8) tail on the C-terminus and a 6×-His tag (or other purification tags) for later purification. To prepare the heptamers, mutant αHL (M) and αHL monomers without cysteine (WT) can be mixed in different molar ratios (M:WT=1:6-4:3) and allowed to co-assemble on rabbit erythrocyte membranes (rRBCMs) or liposomes. Membranes then can be solubilized in SDS and the heptamers separated on SDS-PAGE due to increased migration of the monomers with the negatively charged D8 tail (αHL heptamers are stable in SDS unless heated). Heptamer pores containing only one mutant monomer ($M_1WT_6$) can be passively eluted from the polyacrylamide with water. Further analysis can be achieved by heating the proteins to 95° C. and separating dissociated subunits in a second analytical gel.

In certain embodiments, generating a single linker per protein could be done by controlling the ratio of protein to linker. Excess amounts of protein will allow for a significant amount of single linker protein (removing the requirement for a single mutant subunit in the heteroheptamer). The protein can then be reacted with the orthogonally tagged magnetic beads, and the magnetic beads can be utilized to separate the tagged protein from the untagged protein that will be present since it was in excess for the reaction with the linker. Alternatively, a single linker could be attached to a magnetic nanoparticle first, then reacted with protein. Magnetic nanoparticles with a single linker are commercially available from Nanopartz (Loveland, CO), and the single linker can be achieved by manipulation of the stoichiometry, or by more sophisticated solid phase exchange reactions.

In some embodiments, a second reader, MspA, is a homo-octameric pore, composed of eight monomers each 184 amino acid in size. Mutations made to MspA have allowed for successful DNA translocation and single base discrimination, as well as immobilization of gold nanoparticles. Tags can be added to MspA, at the periplasmic loop 6 (residues 121-127) and fusion proteins with peptide linkers that linked 2 MspA monomers together (linking the N-terminus of one MspA monomer to the C-terminus of a second MspA monomer) to form a dimer, 4 dimers then assembled to form the functional oligomers. The same approach used with αHL to separate and select readers with a single cysteine can be applied to MspA, as MspA is also able to retain oligomeric assembly in SDS-PAGE. A single point mutation introducing cysteine can be made at the N-terminus located on the exterior of the cis side of the pore. MspA with a single cysteine can then also be reacted with maleimide-containing bifunctional linkers. Alternatively, other biological nanopore readers such as CsgG or OmpF can be similarly modified with cysteine and purification tags on the cis side of the pore and substituted for αHL or MspA.

In certain embodiments, a linker consisting of polyethylene glycol (PEG) or DNA with a cysteine-reactive functional group can then be reacted with the cysteine-modified nanopore readers. In some embodiments, a maleimide-$PEG_{(70-720)}$-biotin bifunctional linker with a length ~25-200 nm places the magnetic particles some distance away from the protein to avoid interference with DNA translocation and sequencing. In some embodiments, a synthetic polymer linker has a length of about 25 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm 180 nm, 190 nm or 200 nm. In some embodiments, as an alternative to a synthetic polymer linker, the reader and nanoparticle can be linked via double-stranded DNA (about 75-600 bp, about 25-200 nm in length). In some embodiments, the double-stranded DNA has a length of about 25 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm 180 nm, 190 nm or 200 nm. In some embodiments, the double-stranded DNA is 75 bp, Single-stranded DNA (ssDNA) can similarly be synthesized with a terminal maleimide modification for ligation to cysteine residues. Alternatively, ssDNA has previously been covalently attached to a single monomer of αHL via a disulfide linkage within the heptameric pore to study DNA duplex formation. Briefly, 5'-thiol-modified DNA oligonucleotide with a hexamethylene linker can be activated with 2,2'-dipyridyl disulfide in order to form 5'-S-thiopyridyl oligonucleotide. αHL, MspA, or other biological nanopore readers containing a single cysteine mutation can then be reacted with activated 5'-S-thiopyridyl oligonucleotide. In some embodiments, if a cysteine label on the nanopore reader is insufficient for attachment to the PEG or DNA linker, an unnatural amino acid can be incorporated into the biological nanopore reader, to convey bioorthogonal reactivity, such as click chemistry, inverse electron demand Diels-Alder cycloaddition and others. For click chemistry in particular, an alkyne or azide unnatural amino acid can be incorporated into the nanopore reader, then reacted with a DNA or PEG linker containing the corresponding azide or alkyne.

In certain embodiments, the other end of the linker can be attached to the magnetic nanoparticle using affinity tags or covalent coupling chemistry. In some embodiments, bifunctional linkers with a cysteine-reactive group described above, and a biotin group on the opposite end can be attached to streptavidin coated magnetic particles (Ocean Nanotech, San Diego, CA) via the strong biotin streptavidin interaction. In other embodiments, other affinity tags, including FLAG and Myc, could be used. In some embodiments, a linker can also be covalently attached by reacting an amine-modified PEG linker directly with carboxylate-modified magnetic particles activated with an EDC reagent. For the DNA tethers, ssDNA complementary to the ssDNA attached to the nanopore reader can contain a terminal biotin-tag for attachment to streptavidin-coated magnetic nanoparticles. The oligonucleotide-modified readers can then hybridize with complementary strands attached to magnetic nanoparticles to link them together. In certain embodiments, the alternative affinity and covalent attachment methods described above can also be used to link ssDNA to biological nanopore readers or magnetic particles.

In certain embodiments, after isolating the assembled readers containing a single cysteine-conjugated linker, a population with a single magnetic particle often is purified. In some embodiments, to minimize the number of particles tagged with multiple readers, the readers with reactive linkers can be incubated with an excess of about 5-500 nm magnetic nanoparticles coated with streptavidin (or other surface modifications). The unbound magnetic nanoparticles and reader-nanoparticle conjugates can be isolated from unbound readers by applying a magnetic field, followed by the purification of the reader-nanoparticle complex by Ni-NTA affinity chromatography (cysteine containing monomers will have a D8 tail and a 6×-His tag). Magnetic particles with no reader attached often are washed off with buffer, then immobilized assemblies are eluted with an imidazole gradient, separating particles that have one His-tagged reader from those that have multiple. Alternatively, in some embodiments, single-tagged particles can be purified using a different tag to the biological nanopore reader (strepII or HA tag), with immobilized anti-αHL/anti-MspA antibodies, or via size exclusion chromatography.

While the description above describes the route and ability to tag or link a biological nanopore reader to a single magnetic particle, in certain embodiments it should be specifically noted that multiple (about 2 to about 100) magnetic particles (about 5 to about 500 nm in diameter) could also be attached to a single reader, in order to be able to influence both their position via a magnetic field in bulk solution as well as within a planar lipid bilayer, black lipid membrane, tri block copolymer, etc.

In any configuration, either using a single magnetic nanoparticle or multiple magnetic nanoparticles, these magnetic particles could be directly attached to the outside of the readers or tethered to the readers. In some embodiments, these tethers can range in length from about 2.5 nm to about 1000 nm in length.

System

In some embodiments, the instrument described herein can include high-impedance, low-noise, amplifiers optimized for measuring low-level currents. In certain embodiments, an amplifier with independent, high-speed, DC bias often is incorporated for each reader electrode. In some embodiments, two amplifiers and two DC bias levels often are incorporated to measure and control a pair of coupled sensors. In some embodiments, the amplifiers often are electrically connected to the reader chip which includes the coupled sensors (see next section). In certain embodiments, the signals often are filtered for protection from aliasing and digitized. In some embodiments, an FPGA often is utilized to run a control protocol for the DC bias levels while a host computer archives and analyzes the data as well as providing high-level control of the instrument.

Chips

In some embodiments, the coupled sensors are sometimes fabricated on a fused quartz/silica substrate that is approximately 0.5 mm thick, but other high-resistivity, low-loss substrates are also appropriate to limit parasitic capacitance (e.g., glass or sapphire). In certain embodiments, the substrate thickness is flexible and could be about 0.1 mm to about 2.0 mm. In some embodiments, a substrate has a thickness of about 0.1 mm, 0.15 mm, 0.2 mm, 0.25 mm, 0.30 mm, 0.35 mm, 0.40 mm, 0.45 mm, 0.50 mm, 0.55 mm, 0.60 mm, 0.65 mm, 0.70 mm, 0.75 mm, 0.80 mm, 0.85 mm, 0.90 mm, 0.95 mm, 1.00 mm, 1.10 mm, 1.15 mm, 1.20 mm, 1.25 mm, 1.30 mm, 1.35 mm, 1.40 mm, 1.45 mm, 1.50 mm, 1.55 mm, 1.60 mm, 1.65 mm, 1.70 mm, 1.75 mm, 1.80 mm, 1.85 mm, 1.90 mm, 1.95 mm or 2.00 mm. The substrate with electrodes, contacts, interconnects, and insulative layer is referred to as a chip. In certain embodiments, a substrate is a base structure of a chip onto which a chip is built. In some embodiments, a chip can have a single coupled sensor site or thousands of coupled sensor sites. In certain embodiments, a coupled sensor site can include two electrodes comprised of metals such as Pt, Au, or Ag in close proximity to each other, e.g., about 100 nm to about 10,000 nm. In certain embodiments, electrodes are at a distance of about 100 nm, 200 nm, 300 nm, 400 nm, 500 nm, 600 nm, 700 nm, 800 nm, 900 nm, 1000 nm or up to 10,000 nm from each other. In certain embodiments, one or multiple larger electrodes may be included to form reference electrodes for the bath, but COTS external reference electrodes can be utilized. In some embodiments, variants with multiple reference electrodes may include different metals such as one electrode Pt and the other Ag for example. In some embodiments, the Ag electrode variant chips may be treated to form stable Ag/AgCl electrodes. In some embodiments, electrodes are connected to contact pads comprising Au or Pt on the periphery of the chip to connect the chip to the measurement system. In certain embodiments, a chip is covered with about a 1-100 micrometer thick polymer insulator, such as SU-8, polyimide, parlylene, or PTFE but other coatings that meet the specific requirements of chemical compatibility, insulative, and low-loss that are acceptable. In some embodiments, a polymer insulator has a thickness of about 1 μm, 2 μm, 5 μm, 10 μm, 20 μm, 30 μm, 40 μm, 50 μm, 60 μm, 70 μm, 80 μm, 90 μm, or 100 μm. In certain embodiments, an insulative layer is patterned and etched in a manner to expose all the electrodes and contacts, thus creating openings over the electrodes and access to the contact pads. In some embodiments, the openings are then enlarged using thin-film processes, e.g. etching or ion milling, such that for a given coupled sensor site the minimum distance between the perimeter of one well to the perimeter of another well be about 10 nm to about 10,000 nm. In certain embodiments, a distance between the perimeter of one well to the perimeter of another well is about 10 nm to about 1000 nm. In some embodiments, a distance between the perimeter of one well to the perimeter of another well is about 10 nm, 50 nm, 100 nm, 200 nm, 300 nm, 400 nm, 500 nm, 600 nm, 700 nm, 800 nm, 900 nm, 1000 nm, 2000 nm, or 10,000 nm. These openings define the shape of the wells or PLB cavity shape.

Figure 5A:
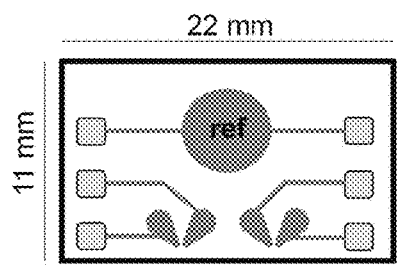
FIGS. 5A-C show a schematic of a two-plex dual biological-nanopore-based sequencing chip (not drawn to scale).
Figure 5B:
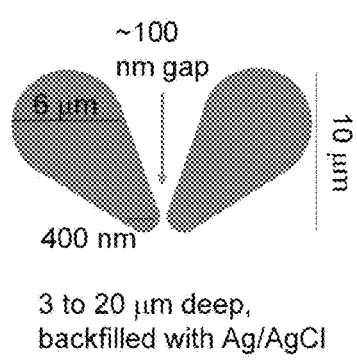
Figure 5C:
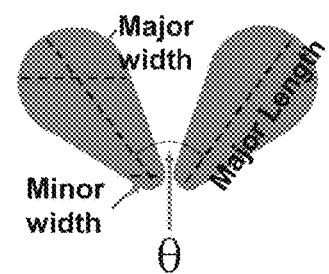

The shape of the PLB cavity is not arbitrary and operates in conjunction with an applied magnetic field to guide the reader pore to the required measurement site. The example shown in FIGS. 5A-C shows a tilted snowcone shaped PLB cavity structure. The logic behind this concept is that the wider region having a 6 micrometers wide dimension, for example, provides a large insertion area for the reader pores whereas the smaller region having a 400 nm dimension, for example, confines the reader pore to the measurement area, i.e. the DNA capture zone. In some embodiments, a dimension for the smaller region can be fabrication process and bilayer formation dependent. In some embodiments, a dimension for the smaller region can be about 50 nm to about 1000 nm. In certain embodiments, a dimension for a smaller region is about 50 nm, 100 nm, 150 nm, 200 nm, 250 nm, 300 nm, 350 nm, 400 nm, 450 nm, 500 nm or 1000 nm. In some embodiments, a dimension for a smaller region is about 50 nm, 100 nm, 150 nm, 200 nm or 250 nm. In some embodiments, this concept also allows larger electrodes to be utilized, which last longer for Ag/AgCl electrodes and have a lower impedance.

In certain embodiments, this concept also allows large long lasting electrodes to be formed and utilized. A magnetic field is applied to the structure to produce a field gradient as shown in FIG. 2B. The gradient in the magnetic field is then coupled to the magnetic nanoparticle tagged reader pore to pull the reader pore into the narrow section of the snowcone shaped PLB, using the shape of the PLB cavity as a guide. In some embodiments, application of the magnetic field can drive the two reader pores (i.e., one pore in each well) to within about 10 nm to about 5 μm of each other. In some embodiments, application of the magnetic field can drive the two reader pores (i.e., one pore in each well) to within a few hundred nanometers of each other. In certain embodiments, application of the magnetic field can drive the two reader pores (i.e., one pore in each well) to within about 10 nm, 50 nm, 100 nm, 200 nm, 300 nm, 400 nm, 500 nm, or 1000 nm of each other. In certain embodiments, other cavity shapes can be utilized, such as shapes that include a region having a larger surface area than another region within the shape. Non-limiting examples include football, triangular, diamond, crescent, oval, lightbulb, skull, and pill shapes. In certain embodiments, cavity shapes include snowcone, football, teardrop, bullet, triangle, curvilinear triangle, crescent, circle, oval, ellipse, parabola, hyperbola, annulus, lens, circular segment, circular sector, heart, trefoil, quatrefoil, lightbulb, skull, pill, polygon, quadrilateral, star, diamond, trapezoid, square or rectangle. In some embodiments, the two adjacent cavities or wells often are tilted towards one another. This tilted configuration permits a first region in one well having a smaller surface area, or the smallest surface area, to be located in close proximity to a second region in the other well having a smaller surface area, or the smallest surface area. Each well can be viewed as having a major (long) virtual axis parallel to the major length of the well. For wells that are tilted towards one another the long virtual axis of a first well is at an angle between about 2 degrees and about 170 degrees with respect to the long virtual axis of the second well, where an angle of 0 degrees is defined as the long virtual axis of each well-being parallel to one another and an angle of 90 degrees is defined as the long virtual axis of each well-being perpendicular to one another. In certain embodiments, the long virtual axis of a first well is at an angle of about 2 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees or 120 degrees with respect to the long virtual axis of the second well. In some embodiments, the long virtual axis of a first well is at an angle of about 5 degrees to about 120 degrees with respect to the long virtual axis of the second well.

In some embodiments, the well opening shape and the tilt of the wells often are selected such that the width of the opening of each well decreases as the distance between the wells decreases. In some embodiments, the shape of the first well and the shape of the second well are the same. In some embodiments, the shape of the first well and the shape of the second well are different.

In some embodiments, the chip may also include thin film magnetic microstructure circuits to concentrate the flux around the cavities and generate large magnetic field gradients in localized regions. In certain embodiments, the magnetic circuits may be fabricated on a second chip that is either bonded to the sensor chip or placed below it in the test fixture. In some embodiments, the magnetic microstructures could be fabricated using thin film processes and materials with high relative permeabilities such as but not limited to Ni, Fe, or Co. In certain embodiments, these structures can be made small (about 1 to about 100 um) and localized around the cavity/PLB using thin film processes and lithography. In certain embodiments, they may include long strips of magnetic material that span several or all coupled sensors on a chip (FIG. 8A) or magnetic structures localized to a specific coupled sensor pair (FIG. 8B). In some embodiments, the magnetic microstructure circuits can be energized with an electromagnet near the magnetic microstructure (e.g. within a distance of about 1 mm, 2 mm, 5 mm, 10 mm, 15 mm, or 25 mm) or by bringing the core of the electromagnet into contact with the microstructure tabs. A permanent magnet (e.g., rare-earth magnet) would similarly work for energizing the magnetic microstructure circuit. Due to the high magnetic field gradient generated near small paramagnetic structures, smaller electromagnet coils or permanent magnets can be used with these microstructures.

Magnetic Field Application

In some embodiments, an external magnetic field can be applied to induce magnetophoresis of magnetic nanoparticles. In certain embodiments, the magnetic field can be applied with an external permanent magnet or coil (FIGS. 6A and 6B), or thin film microstructured magnetic circuits (i.e., not a magnet but a high permeability material) or coils fabricated into a chip.

Figure 7C:
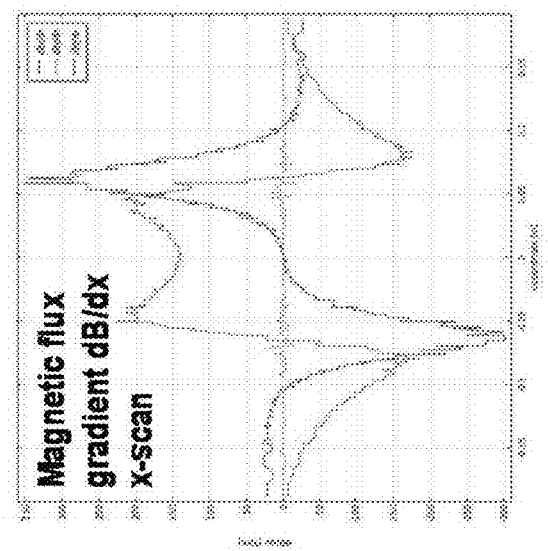
FIGS. 7A-C illustrate finite element models of the magnetic flux density distribution surrounding rare-earth permanent magnets.
Figure 7B:
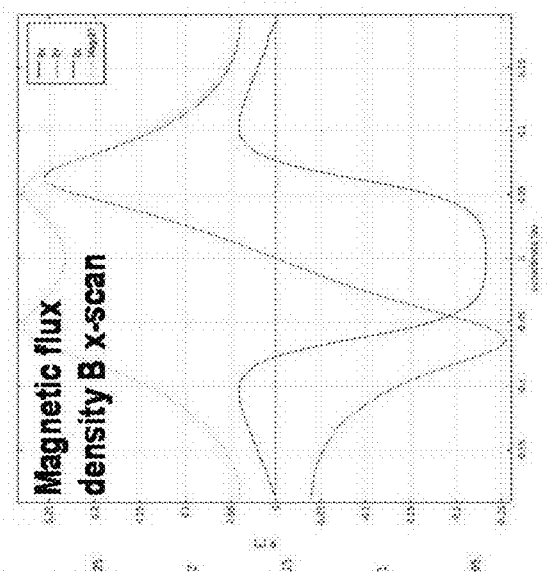
Figure 7A:
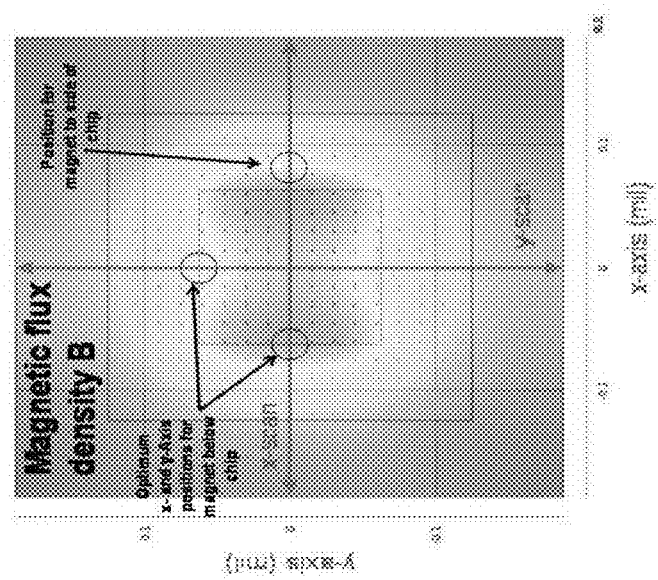

In certain embodiments, a chip reader instrument sometimes includes a permanent magnet that can be positioned a variable distance from the chip edge. In some embodiments, the distance is about 1 mm, 2 mm, 3 mm, 5 mm, 10 mm, 12.5 mm, 15 mm, 20 mm, 25 mm, 30 mm, 35 mm, 40 mm, 45 mm, 50 mm, 100 mm, 200 mm or 500 mm from the edge of the chip. This configuration allows for fine tuning of the field gradient. In certain embodiments, the instrument can also accommodate a variety of permanent magnet sizes as necessary. In some embodiments, the magnets can be oriented horizontally to the side of the chip for a brute force approach as shown in FIGS. 8A and 8B, or can be oriented below the chip for a more localized region of high gradient, for example. FIGS. 7A-7C show the field characteristics as generated by finite element analysis for a small permanent magnet underneath the chip. The gradients are much larger compared to a more powerful magnet placed on the side of the chip. This is because the magnet underneath the chip couples better to the surface of the chip.

Alternatively, in certain embodiments, a wire coil electromagnet near the chip can be used to apply the external magnetic field. By applying current to the electromagnetic coil the magnetic field can be toggled on, off, adjusted continuously, or modulated with an external signal to provide fine manipulation of magnetic particles. In some embodiments, the electromagnet often includes a wire coil close to the chip reader apparatus on a fixed mount. In some embodiments, the coil may be placed on the side (FIG. 6B) or bottom of the chip reader device.

In certain embodiments, another option is to fabricate a microstructure magnetic circuit out of thin sheets of high permeability material such as mu-metal or Metglas alloys. In some embodiments, the sheets of material could be laser cut or chemically etched (Fotofab, LLC, Chicago, IL) with the desired pattern and placed below the chip, or even bonded to the underside of the chip directly. Although features are not as small as with thin film processes they may still be sufficient for features in the 25-500 um range. Considering that in certain embodiments the substrate is about 0.5 mm thick the microstructure will couple strongly to the PLB cavity. In some embodiments, the microstructures can be energized with an electromagnet by bringing the core of the electromagnet into contact with the microstructure as mentioned previously.

FPGA Capture and Control

In order to sequence a polymer on the adjacent-dual-biological-nanopore-based sequencing platform, a nanopore reader is associated with each well of the chip. In certain embodiments, a reader can be associated with each well of the chip using the following non-limiting example of a manufacturing process. The chip is initially bathed within an electrolyte solution or bath. A PLB then is formed over each PLB cavity on the chip, using known methods to paint or cast thin films of membrane-forming materials over the PLB cavity. In some embodiments, the individual nanopore readers utilized then are inserted into each target PLB, utilizing a voltage cycling process (see U.S. Pat. No. 8,968,539). Any configuration of biological nanopore readers can be used for sequencing. In certain embodiments, two αHL pores, two MspA pores, αHL pore plus MspA pore, or MspA pore plus CsG pore may be utilized, with typically one pore in one PLB in one well. In some embodiments, the nanopore readers can be of the same type, different types or the same type with one reader being wild-type and the other reader mutated, engineered, and/or chemically modified or both readers mutated, engineered, and/or chemically modified differently. The combination of readers will depend on the information that is desired from the sequencing application, and the combinations of readers could be chosen to provide the most complementary data on the polymer that is being sequenced.

Once the individual readers are present within each PLB, a magnetic field is applied to the chip in order to draw each magnetic nanoparticle tagged reader pore into close proximity of one other. An overview of this example of reader insertion and manipulation with a magnetic field is shown in FIGS. 9A-9E, and a PLB formation and reader insertion protocol with applied voltages is shown in FIGS. 10A-10E, for example. While a PLB is referred to here over each well, any suitable seal capable of retaining an individual reader can be utilized, including but not limited to a seal comprising phospholipids (e.g. DPhPC, POPC, DOPC, DMPC, DoPhPC), surfactants, di-block copolymers (e.g. polybutadiene-polyethylene oxide), tri-block copolymers (e.g. poly-2-methyl-2-oxazolinepolydimethylsiloxane-poly-2-methyl-2-oxazoline), or polymerizable versions thereof.

After the reader pores have been inserted and have been magnetically moved to their measurement sites the DNA, RNA, protein or peptide sample often is added to the bath. In certain embodiments, a FPGA often is used to control the capture protocol, shown in FIGS. 11A-11E, similar to the following:

1. Set bias with respect to the bath reference electrode on one of the PLB electrodes (PLB1) to a positive level (e.g. +100 mV to +250 mV) in order to capture one end of the polymer, while the other PLB electrode (PLB2) is set near zero or negative (e.g. −60 mV to +60 mV) to prevent entry.
2. Monitor the current on PLB1 for capture of the single stranded polymer which will be registered by a decrease the current.
3. Once captured the bias protocol is reversed whereas PLB1 bias level is set to near zero or negative (e.g. −60 mV to +60 mV) to prevent rapid translocation into well 1, and PLB2 is set to a positive level (e.g. +100 mV to +250 mV) in order capture the free uncaptured end of the polymer into well 2.
4. Monitor the current on PLB2 for capture of the free end of the single stranded polymer which will be registered by a decrease the current.
5. Once captured both bias levels can be set to the same or similar low voltage (−150 mV to +150 mV) to prevent escape of the polymer.

With both ends of the polymer captured the FPGA can run the measurement protocol to thread the polymer back and forth through the two reader pores. This will be done by setting both the bias on PLB1 and PLB2 with respect to the bath reference such that one acts as the drive voltage and the other functions as a "brake," i.e. driving both captured ends of the polymer into each well, with one directionality overcoming the other. For example, if both electrodes are set to ~+100 mV, based on the translocation kinetics of the utilized readers, the polymer will be quasi-stationary (because of DC offsets on the electrodes). However, if the PLB1 electrode is set +100 mV and the PLB2 electrode is set to +50 mV there will be a net force pulling the polymer into the PLB1 cavity. The current measured from the PLB1 cavity will be with respect to the +100 mV bias but the translocation through the reader pore will be slower than a free polymer with +100 mV bias because PLB2 is pulling back on the polymer. Once the polymer is driven through one of the readers against the applied bias pulling the polymer in the direction of the other reader, and sequenced, before the polymer is fully pulled out and escapes from that other reader, the FPGA can trigger a reversal of the applied biases to drive the polymer back through that other reader, against the applied bias pulling the polymer in the direction of the reader that it was originally driven through. This would enable the polymer to be first sequenced though one of the readers and then sequenced through the other reader, while maintaining capture of the polymer via both readers. This multipassing or flossing strategy, all while maintaining capture of the polymer by both adjacent readers, can be carried out between 2 to 10,000 times. In some embodiments, multipassing can be 2, 3, 5, 10, 20, 50, or 100 times, with the number of multipasses increasing in a linear or exponential manner in order to make replicate measurements and improve the quality of the sequencing data to a desired level by e.g. increasing base calling accuracy, decreasing error rates or deletions or insertions, improving detection of modified nucleobases.

In some embodiments, during any of these voltage control steps an applied bias of −1 V to 1 V could be utilized, with an optimal voltage range being about −220 mV to about +220 mV. In certain embodiments, the voltage range can be about −220 mv, −210 mv, −200 mv, −190 mv, −180 mv, −170 mv, −160 mv, −150 mv, −140 mv, −120 mv, −100 mv, −90 mv, −80 mv, −70 mv, −60 mv, −50 mv, −40 mv, −30 mv, −20 mv, −10 mv, +10 mv, +20 mv, +30 mv, +40 mv, +50 mv, +60 mv, +70 mv, +80 mv, +90 mv, +100 mv, +110 mv, +120 mv, +130 mv, +140 mv, +150 mv, +160 mv, +170 mv, +180 mv, +190 mv, +200 mv, +210 mv or +220 mv, with the magnitude of the voltage being used to control the tension of the captured polymer and the difference in the voltage between the PLBs controlling the translocation velocity.

In certain embodiments, alternative versions of this dual polymer strand capture and sequencing include:
A. Setting both electrode biases to positive and capturing 1 end of the polymer via one reader and the other end of the polymer via the other reader simultaneously or in a similar timeframe, and then setting the biases to control the rate and directionality of strand translocation.
B. Driving the polymer all the way into one of the wells through one of the readers and then driving it out and capturing the end that exits via the other reader.

In certain embodiments, triggers that can be used to automatically or semi-automatically switch the applied biases and drive the polymer in the opposite direction inducing multipassing or flossing of the polymer through the two readers include, but are not limited to:
I. Set periods of time
II. Exit signatures of the end of the polymer coming out of one of the readers, before fully escaping out into bulk
III. Specific sequences of the polymer
IV. Molecular markers added to the polymer at specific or arbitrary locations in the form of adducts Additional Alternatives In some embodiments, it may be appropriate to use a reader capable of sequencing a polymer in one of the PLBs and a large opening channel or pore, which is not capable of sequencing, in the other PLB. This large opening pore, with an opening and/or channel diameter of about 4 nm to about 50 nm wide could be used to increase the initial capture efficiency of the one end of the polymer, before then capturing the other end of the polymer with the reader. In this case the pore with the larger opening would be used as the initial capture side and serve as the brakes/translocation control of the system, while the other pore/reader would be used to sequence the polymer strand. In some embodiments, it may be appropriate to first capture the polymer with the reader, before then capturing the other end of the polymer with the large open pore. This case would be appropriate when capture of the polymer by the reader is efficient, but capture of the other end of the polymer by the second reader is inefficient or slow. In this case, the pore with the larger opening would serve as the brakes/translocation control while the reader would be used to sequence the polymer.

In certain embodiments, it may be appropriate to use the current signature of the reader, to sequence the polymer, as the polymer is translocating through the reader into the well in which that reader resides. In some embodiments, it may be appropriate to use the current signature of the reader, to sequence the polymer, as the polymer is translocating back out of the reader, out of the well in which that reader resides, in the direction of the other reader or well. In certain embodiments, it may be appropriate to sequence the polymer in both translocation directions through both readers or any combination thereof. In certain embodiments, polymer sequence determination from any of these translocation directions or configurations, as well as from multipass or flossing reads of the polymer, can then be used in combination with one another to determine the sequence of the polymer with a higher accuracy, than any single pass sequence determination would allow for individually.

In certain embodiments, it may be appropriate to sequence the polymer with a single pass. In certain embodiments, it may be appropriate to sequence the polymer with multiple passes. In some embodiments, it may be appropriate to capture the polymer with both adjacent readers and then drive and sequence the polymer all the way through one of the readers completely into the well in which that reader resides. Once fully captured in that well, one of the ends of the polymer can be translocated back out of the well and that end of the polymer can be captured by the other reader, recapturing that polymer strand across both adjacent readers. The polymer strand could then be driven and sequenced all the way through the other reader completely into the other well. This process could then be carried out multiple times: capture of the polymer with both readers, driving and sequencing the polymer all the way through one of the readers, capture of the polymer with both readers, driving and sequencing the polymer all the way through the other reader, repeat. In some embodiments, it may be appropriate to utilize adjacent wells that have the same shape or a symmetric shape. In some embodiments, it may be appropriate to utilized adjacent wells that have different shapes.

In some embodiments, it may be appropriate to sequence double-stranded DNA (dsDNA) or double-stranded RNA (dsRNA) by the dual-biological-nanopore-based sequencing platform. In this case the opening of the nanopore reader and its inner diameter of the lumen have to be wide enough to be able to capture and translocate the double-stranded polymer, but also have a sensing region capable of resolving molecular features of the analyte, i.e. the reader must be capable of sequencing double stranded DNA or RNA. Given the diameter of dsDNA helix reported at 2 nm, such nanopore readers should have the inner diameter larger than about 2 nm.

Sequencing of Proteins and Peptides

In certain embodiments, other biopolymers like proteins or peptides may also be sequenced. In some embodiments, the C-terminus of the protein or peptide (modified or unmodified with a linker or tag) can be first captured by the reader in PLB 1 and held, followed by capture of the N-terminus (modified or unmodified with a linker or tag) by the reader in PLB 2, or vice versa. After capture of one end in PLB 1, the voltage can be reduced to hold the protein or peptide in place while the other end of the protein or peptide is captured in PLB 2. After dual capture, the voltage will be increased to a high level (e.g. +−220 mV) in both PLBs to denature the protein or peptide secondary structure and stretch it between the readers in the PLBs. Next, the voltage may be controlled using the FPGA capture and control system to pass the peptide or protein between the two readers. In certain embodiments, as the protein or peptide passes through the reader, the sequence will be read via the blocking current levels, translocation time, and/or current noise of the amino acids within the readers. In some embodiments, proteins and peptides may be multipassed between 1 and 1000 times. In certain embodiments, proteins and peptides may be multipassed 1, 2, 5, 10, 20, 50, or 100 times to achieve the desired level of residue identification accuracy. Because proteins and peptides do not have a polymer backbone with intrinsic charge like DNA and RNA, their net charge may vary significantly based on their amino acid content. In certain embodiments, the C- and N-termini of the protein or peptide may be first ligated to a charged polymer to increase its charge density and facilitate electrophoretic capture and translocation through the reader. In some embodiments, this polymer may be, but is not limited to a polypeptide (e.g. polyarginine, polylysine, polyglutamate), a DNA polymer, an abasic DNA homopolymer, or a synthetic polymer (e.g. polystyrene sulfonate, polyallylamine, polyacrylate, polyvinyl sulfonate). In some embodiments, the length of a homopolymer may vary from about 5 to about 10000 monomer units. In certain embodiments, the length is between about 100 and about 1000 monomer units, with the length chosen to facilitate high ligation coupling yield and high capture rates by the readers. Alternatively, in some embodiments charged surfactants (e.g., sodium dodecyl sulfate) may be added to the fluid to increase the charge density of the protein or peptide via adsorption to facilitate capture and translocation through the readers. The added surfactant also serves to denature the protein or peptide secondary structure, facilitating unfolding, stretching, and translocation through the readers. In some embodiments, alternatively, or in addition to surfactants, other denaturants including but not limited to urea or guanidinium chloride may be added to the fluid to denature the protein or peptide secondary structure to facilitate unfolding, stretching, and translocation through the readers.

EXAMPLES

The examples set forth below illustrate certain implementations and do not limit the technology.

Example 1: Listing of Certain Embodiments

Provided hereafter is a listing of certain non-limiting examples of embodiments of the technology.

A1. A device, comprising: a chip comprising two adjacent wells separated by a distance, each of the wells comprising an opening aperture, a bottom and an electrode disposed at the bottom.

A2. The device of embodiment A1, wherein the chip comprises a substrate.

A3. The device of embodiment A1 or embodiment A2, comprising:
  a separate seal over the opening aperture of each of the wells;
  a transmembrane channel polymer reader in each seal;
  a first component configured to apply a magnetic field across the wells; and
  a second component configured to detect an interaction between each reader and a
  molecule that can be introduced to the device and contacted by the reader.

A4. The device of embodiment A3, wherein:
  each reader independently is linked to one or more magnetic particles; and
  the particles optionally have an average diameter of about 5 nanometers to about 500 nanometers.

A5. The device of embodiment A3 or embodiment A4, wherein the second component comprises a controllable voltage source configured to quantify DC current and/or AC current.

A6. The device of any one of embodiments A3-A5, wherein the second component is configured to quantify a change in conductance of the reader, thereby permitting detection of an interaction between the molecule and the reader.

A7. The device of any one of embodiments A3-A6, wherein each seal comprises a membrane capable of retaining the reader.

A8. The device of any one of embodiments A3-A7, wherein each seal independently comprises a planar lipid bilayer, surfactant bilayer, deblock copolymer bilayer or triblock copolymer monolayer.

A9. The device of any one of embodiments A3-A8, wherein each reader independently is chosen from a biological nanopore, an ion channel, a transmembrane protein or an engineered DNA or peptide nanopore.

A10. The device of any one of embodiments A3-A8, wherein each reader independently is chosen from alpha-hemolysin (αHL), aerolysin, *Mycobacterium smegmatis* porin A (MspA), *Escherichia coli* CsgG, cytolysin A (ClyA), or outer membrane protein F (OmpF).

A10.1. The device of embodiment A10, wherein one reader is alpha-hemolysin (αHL) and one reader is *Mycobacterium smegmatis* porin A (MspA).

A11. The device of any one of embodiments A3-A10.1, wherein the molecule is a polymer that can be translocated by each reader.

A12. The device of embodiment A11, wherein the polymer is a nucleic acid.

A13. The device of embodiment A12, wherein the nucleic acid is single-stranded RNA or single-stranded DNA.

A13.1. The device of embodiment A12, wherein the nucleic acid is double-stranded RNA or double-stranded DNA.

A13.2. The device of embodiment A11, wherein the polymer is a protein or a peptide.

A14. The device of any one of embodiments A3-A13.2, wherein each electrode independently comprises Au, Ag, Ag/AgCl, Pt, or a combination thereof.

A15. The device of any one of embodiments A3-A14, wherein the chip comprises Si, SiN, $Si_3N_4$, $SiO_2$, glass, quartz, aluminum, sapphire, kapton, parylene, polyimide, diamond, fused silica, SU-8, a photoresist, or a combination thereof.

A16. The device of any one of embodiments A3-A15, wherein:
  the chip comprises a modification that alters a property of an unmodified chip, and
  the modification is configured to:
    aid in the ability to wet the inside of the chip,
    alter an electrical property of the chip,
    aid seal formation and stability,
    limit or prevent non-specific adsorption, alter or remove charge associated with the walls of the chip, or combination of the foregoing.

A17. The device of any one of embodiments A3-A16 wherein each well independently comprises a depth from the opening aperture to the electrode of about 2 micrometers to about 100 micrometers.

A18. The device of any one of embodiments A3-A17, wherein the surface area of the opening aperture of each of the wells independently is about $7.0 \times 10^{-13}$ $m^2$ to about $8.0 \times 10^{-9}$ $m^2$.

A18.1. The device of any one of embodiments A3-A17, wherein the diameter of the opening aperture of each of the wells is about 1 to about 100 um.

A19. The device of any one of embodiments A3-A18.1 wherein:
- each of the wells comprises a major length and a virtual major axis parallel to the major length, and
- the virtual major axis of one of the wells is disposed at an angle of about 5 degrees to about 120 degrees with respect to the virtual major axis of the other well.

A20. The device of embodiment A19, wherein:
- each of the wells comprises a minor width and a major width, and
- the width of each of the wells narrows from the major width to the minor width as the distance between the wells decreases.

A21. The device of any one of embodiments A3-A20, wherein the opening aperture of each of the wells independently comprises a perimeter comprising one or more of a straight line, curved line or point.

A22. The device of embodiment A21, wherein the opening aperture of each of the wells independently comprises a perimeter shape defined by a snowcone, football, teardrop, bullet, triangle, curvilinear triangle, crescent, circle, oval, ellipse, parabola, hyperbola, annulus, lens, circular segment, circular sector, heart, trefoil, quatrefoil, lightbulb, skull, pill, polygon, quadrilateral, star, diamond, trapezoid, square or rectangle.

A23. The device of any one of embodiments A20-A22, wherein:
- each reader is tethered independently to one or more magnetic particles, and
- the first component is configured to move via a magnetic force each reader in the direction of a region of each of the wells defined by the minor width.

A24. The device of any one of embodiments A3-A23, comprising a fluid bathing the chip.

A25. The device of embodiment A24, wherein the fluid comprises an ionic solution or an aqueous solution comprising a buffered electrolyte.

A26. The device of any one of embodiments A1-A25, wherein the distance between the closest points between the opening apertures of the wells is about 1 nanometer to about 50 micrometers.

A27. The device of embodiment A26, wherein the distance between the closest points between the opening apertures of the wells is about 100 nanometers.

A28. A multiplex device, comprising two or more of the devices of any one of embodiments A1-A27.

B1. A device, comprising: a nanopore reader tethered to one or more nanoparticles.

C1. A method for determining a polymer sequence, comprising:
- (a) contacting a fluid containing a polymer comprising monomeric units, a first end and a second end, with a device comprising:
  - a chip,
  - a first well disposed adjacent to a second well on the chip,
  - a first seal over the first well and a second seal over the second well, and
  - a first reader in the first seal and a second reader in the second seal, wherein the
  - first reader and the second reader each is a nanopore reader;
- (b) electrophoretically and/or electroosmotically driving the first end of the polymer from the fluid through the first reader into the first well; thereby capturing the first end of the polymer by the first reader;
- (c) electrophoretically and/or electroosmotically driving the second end of the polymer in the fluid through the second reader into the second well; thereby capturing the second end of the polymer by the second reader;
- (d) after part (c), electrophoretically driving at least a portion of the polymer through the first reader into the first well or through the second reader into the second well; and
- (e) identifying monomeric units of the polymer based on a current signature of each of the monomeric units, translocation time and/or associated current noise level modulation as the polymer translocates through the first reader or the second reader in part (d), thereby determining the sequence of the polymer.

C2. The method of embodiment C1, wherein the polymer is a single-stranded molecule.

C3. The method of embodiment C2, wherein the polymer is single-stranded DNA or single-stranded RNA.

C3.1. The method of embodiment C1, wherein the polymer is double-stranded DNA or double-stranded RNA.

C3.2. The method of embodiment C1, wherein the polymer is a protein or a peptide.

C3.3. The method of any one of embodiments C1-C3.2, wherein the nanopore reader is a transmembrane channel polymer reader.

C4. The method of any one of embodiments C1-C3.3, wherein after part (d):
- a portion of the polymer is in contact with the second reader after the polymer is electrophoretically driven through the first reader into the first well, or
- a portion of the polymer is in contact with the first reader after the polymer is electrophoretically driven through the second reader into the second well.

C5. The method of any one of embodiments C1-C4, wherein:
- part (b), part (c) and/or part (d) comprises applying a voltage bias, and
- part (b), part (c) and/or part (d) comprises adjusting the applied voltage bias.

C6. The method of embodiment C5, wherein part (b), part (c) and/or part (d) comprises decreasing the applied voltage bias after capturing the polymer.

C7. The method of embodiment C5 or embodiment C6, wherein part (d) comprises adjusting voltage bias, wherein the voltage bias is sufficient to:
- electrophoretically drive at least a portion of the polymer through the first reader into the first well and overcome the voltage bias used to drive at least a portion of the polymer in the direction of the second reader in part (c), or
- electrophoretically drive at least a portion of the polymer through the second reader into the second well and overcome the voltage bias used to drive at least a portion of the polymer in the direction of the first reader in part (b).

C8. The method of any one of embodiments C1-C7, comprising, after part (e) performing part (d') and part (e'):
(d') electrophoretically driving at least a portion of the polymer through the first reader into the first well if the polymer was driven into the second well in part (d), or electrophoretically driving at least a portion of the polymer through the second reader into the second well if the polymer was driven into the first well in part (d); and
(e') identifying monomeric units of the polymer based on a current signature of each of the monomeric units, translocation time and/or associated current noise level modulation as the polymer translocates through the first reader or the second reader in part (d'), thereby determining the sequence of the polymer.

C9. The method of embodiment C8, wherein part (d') comprises adjusting voltage bias, wherein the voltage bias is sufficient to:
electrophoretically drive at least a portion of the polymer through the first reader into the first well if the polymer was driven into the second reader in part (d), and overcome a voltage bias used to drive at least a portion of the polymer in the direction of the second reader, or electrophoretically drive at least a portion the polymer through the second reader into the second well if the polymer was driven into the first reader in part (d), and overcome a voltage bias used to drive at least a portion of the polymer in the direction of the first reader.

C10. The method of embodiment C8 or embodiment C9, wherein after part (d'):
a portion of the polymer is in contact with the second reader after the polymer is electrophoretically driven through the first reader into the first well, or a portion of the polymer is in contact with the first reader after the polymer is electrophoretically driven through the second reader into the second well.

C11. The method of any one of embodiments C8-C10 comprising repeating parts (d) and (e) after performing parts (d') and (e').

C12. The method of embodiment C11 comprising repeating parts (d') and (e') after repeating parts (d) and (e).

C13. The method of any one of embodiments C8-C12, wherein parts (d) and (e) are performed alternately with parts (d') and (e') about 4 to about 10,000 times.

C14. The method of any one of embodiments C8-C13, wherein in part (d) and/or part (d') the entire polymer is electrophoretically driven through the first reader into the first well or through the second reader into the second well.

C15. The method of any one of embodiments C1-C15, wherein the first reader is linked to one or more magnetic particles, or the second reader is linked to one or more magnetic particles, or the first reader and the second reader each is independently linked to one or more magnetic particles.

C16. The method of any one of embodiments C1-C15, wherein:
the chip comprises a side,
each of the wells comprises a major length, and
the major length of each of the wells is disposed at an angle of about 5 degrees to about 85 degrees with respect to the side.

C17. The method of embodiment C16, wherein:
each of the wells comprises a minor width and a major width, and
the width of each of the wells narrows from the major width to the minor width as the
distance between the wells decreases.

C18. The method of any one of embodiments C15-C17, comprising applying a magnetic field by a component configured to apply a magnetic field across the wells.

C19. The method of embodiment C18, wherein:
the first reader is linked independently to one or more magnetic particles and the magnetic field is of a strength sufficient to move via a magnetic force the first reader in the first seal after the field is applied; and/or
the second reader is linked independently to one or more magnetic particles and the magnetic field is of a strength sufficient to move via a magnetic force the second reader in the second seal after the field is applied.

C20. The method of any one of embodiments C17-C19, wherein the first reader and/or the second reader move via a magnetic force in the direction of a region of each of the wells defined by the minor width.

C21. The method of any one of embodiments C17-C20, wherein the device is a device of any one of embodiments A1-A29.

D1. A device, comprising:
a chip comprising two adjacent wells separated by a distance, each of the wells comprising an opening aperture, a bottom and an electrode disposed at the bottom;
a separate seal over the opening aperture of each of the wells;
a nanopore reader in each seal, wherein each reader independently is tethered to one or more magnetic particles;
a first component configured to apply a magnetic field across the wells; and
a second component configured to detect an interaction between each reader and a molecule that can be introduced to the device and contacted by the reader.

D2. The device of embodiment D1, wherein the chip comprises a substrate.

D3. The device of embodiment D1 or embodiment D2, wherein the magnetic particles are magnetic nanoparticles having an average diameter of about 5 nanometers to about 500 nanometers.

D4. The device of any one of embodiments D1-D3, wherein the nanopore readers in the separate adjacent seals of the chip are magnetically positioned in their respective seals at a distance of about 10 nm to 5 um from each other.

D4.1. The device of any one of embodiments D1-D4, wherein the separation distance of separate seals is about 10 nm, 50 nm, 100 nm, 200 nm, 300 nm, 500 nm, or 1000 nm.

D5. The device of any one of embodiments D1-D4.1, wherein the second component comprises a controllable voltage source configured to quantify DC current and/or AC current.

D6. The device of any one of embodiments D1-D5, wherein the second component is configured to quantify a change in conductance of the reader, thereby permitting detection of an interaction between the molecule and the reader.

D6.1. The device of embodiment D6, wherein the molecule is a polymer of monomeric units and the quantification of the change in conductance of the reader comprises measuring current signature of each of the monomeric units, translocation time or associated current noise level modulation.

D7. The device of any one of embodiments D1-D6.1, wherein each seal comprises a membrane capable of retaining the reader.

D8. The device of any one of embodiments D1-D7, wherein each seal independently comprises a planar lipid bilayer, surfactant bilayer, deblock copolymer bilayer or triblock copolymer monolayer.

D9. The device of any one of embodiments D1-D8, wherein each reader independently is chosen from a biological nanopore, an ion channel, a transmembrane protein or an engineered DNA or peptide nanopore.

D10. The device of any one of embodiments D1-D8, wherein each reader independently is chosen from alpha-hemolysin (αHL), aerolysin, *Mycobacterium smegmatis* porin A (MspA), *Escherichia coli* CsgG, cytolysin A (ClyA), or outer membrane protein F (OmpF).

D10.1. The device of any one of embodiments D1 to D10, wherein the first and second readers are the same.

D10.2. The device of any one of embodiments D1 to D10, wherein the first and second readers are different.

D10.3. The device of embodiment D10, wherein one reader is alpha-hemolysin (αHL) and one reader is *Mycobacterium smegmatis* porin A (MspA).

D11. The device of any one of embodiments D1-D10.3, wherein the molecule is a polymer that can be translocated by each reader.

D12. The device of embodiment D11, wherein the polymer is a nucleic acid.

D13. The device of embodiment D12, wherein the nucleic acid is single-stranded RNA or single-stranded DNA.

D13.1. The device of embodiment D12, wherein the nucleic acid is double-stranded RNA or double-stranded DNA.

D14. The device of embodiment D11, wherein the polymer is a protein or a peptide.

D15. The device of any one of embodiments D1-D14, wherein each electrode independently comprises Au, Ag, Ag/AgCl, Pt, or a combination thereof.

D16. The device of any one of embodiments D1-D15, wherein the chip comprises Si, SiN, $Si_3N_4$, $SiO_2$, glass, quartz, aluminum, sapphire, kapton, parylene, polyimide, diamond, fused silica, SU-8, a photoresist, or a combination thereof.

D17. The device of any one of embodiments D1-D16, wherein:
the chip comprises a modification that alters a property of an unmodified chip, and
the modification is configured to:
aid in the ability to wet the inside of the chip,
alter an electrical property of the chip,
aid seal formation and stability,
limit or prevent non-specific adsorption,
alter or remove charge associated with the walls of the chip, or
combination of the foregoing.

D18. The device of any one of claims D1-D17, wherein each well independently comprises a depth from the opening aperture to the electrode of about 2 micrometers to 100 nanometers.

D18.1. The device of embodiment D18, wherein the depth is about 2, 5, 10, 20, 30, 40, 50, 60, 70, 80, 90, or 100 micrometers.

D19. The device of any one of embodiments D1-D18.1 wherein the surface area of the opening aperture of each of the wells independently is about $7.0 \times 10^{-13}$ $m^2$ to about $8.0 \times 10^{-9}$ $m^2$.

D19.1. The device of any one of embodiments D1-D18.1, wherein the diameter of the opening aperture of each of the wells is about 1 to about 100 um.

D20. The device of any one of embodiments D1-D19.1, wherein the distance between the closest points between the opening apertures of the wells is about 1 nanometer to about 50 micrometers.

D21. The device of embodiment D20, wherein the distance between the closest points between the opening apertures of the wells is about 100 nanometers.

D22. The device of any one of embodiments D1-D21, wherein:
each of the wells comprises a major length and a virtual major axis parallel to the major length, and
the virtual major axis of one of the wells is disposed at an angle of about 5 degrees to about 120 degrees with respect to the virtual major axis of the other well.

D23. The device of embodiment D22, wherein:
each of the wells comprises a minor width and a major width, and
the width of each of the wells narrows from the major width to the minor width as the distance between the wells decreases.

D24. The device of any one of embodiments D1-D23, wherein the opening aperture of each of the wells independently comprises a perimeter comprising one or more of a straight line, curved line or point.

D25. The device of embodiment D24, wherein the opening aperture of each of the wells independently comprises a perimeter shape defined by a snow cone, football, teardrop, bullet triangle, curvilinear triangle, crescent, circle, oval, ellipse, parabola, hyperbola, annulus, lens, circular segment, circular sector, heart, trefoil, quatrefoil, lightbulb, skull, pill, polygon, quadrilateral, star, diamond, trapezoid, square or rectangle.

D26. The device of any one of embodiments D23-D25, wherein: the first component is configured to move via a magnetic force each reader in the direction of a region of each of the wells defined by the minor width.

D27. The device of any one of embodiments D1-D26, comprising a fluid bathing the chip.

D28. The device of claim D27, wherein the fluid comprises an ionic solution or an aqueous solution comprising a buffered electrolyte.

D29. The device of any one of embodiments D1-D28, further comprising FPGA logic in combination with high-speed DC voltage bias switching.

D30. A multiplex device, comprising two or more of the devices of any one of embodiments D1-D29.

E1. A device comprising a nanopore reader tethered to one or more magnetic particles.

E2. The device of embodiment E1, wherein the particles are nanoparticles.

E3. The device of embodiment E1 or embodiment E2, wherein the nanopore reader is tethered to a magnetic particle via a linker.

E4. The device of embodiment E3, wherein the linker has a length and the length is about 25-200 nm.

E5. The device of any one of embodiments E1-E4, wherein the linker is a maleimide-biotin linker.

E6. The device of any one of embodiments E1-E5, wherein the linker is engineered to comprise a cysteine-reactive functional group.

E7. The device of any one of embodiments E1-E4, wherein the linker is a double-stranded DNA linker.

E8. The device of any one of embodiments E1-E7, comprising two nanopore readers.

E9. The device of embodiments E8, wherein the two nanopore readers are each in a planar lipid bilayer.

E10. The device of embodiment E9, wherein the nanopore readers are adjacent to one another and positioned into a dual-capture zone of the planar lipid bilayers.

E11. The device of any one of embodiments E1-E10, comprising an external magnetic field.

F1. A method for determining a polymer sequence or portion thereof, comprising:
- (a) contacting a fluid containing a polymer comprising monomeric units, a first end and a second end, wherein the polymer is a protein or a peptide, with a device comprising:
  a chip,
  a first well disposed adjacent to a second well on the chip,
  a first seal over the first well and a second seal over the second well, and
  a first reader in the first seal and a second reader in the second seal, wherein the first reader and the second reader each is a nanopore reader;
- (b) electrophoretically and/or electroosmotically driving the first end of the polymer from the fluid through the first reader into the first well; thereby capturing the first end of the polymer by the first reader;
- (c) electrophoretically and/or electroosmotically driving the second end of the polymer in the fluid through the second reader into the second well; thereby capturing the second end of the polymer by the second reader;
- (d) after part (c), electrophoretically driving at least a portion of the polymer through the first reader into the first well or through the second reader into the second well; and
- (e) identifying monomeric units of the polymer based on a current signature of each of the monomeric units, translocation time and/or associated current noise level modulation as the polymer translocates through the first reader or the second reader in part (d), thereby determining the sequence of the polymer or a portion thereof.

F2. The method of embodiment F1, wherein the charge of the polymer is modified by attaching charge polymers to the first and second ends of the polymer.

F3. The method of embodiment F1, wherein the charge of the polymer is modified by contacting the polymer with a surfactant.

F4. The method of any one of embodiments F1-F3, wherein after part (d):
- a portion of the polymer is in contact with the second reader after the polymer is electrophoretically driven through the first reader into the first well, or
- a portion of the polymer is in contact with the first reader after the polymer is electrophoretically driven through the second reader into the second well.

F5. The method of any one of embodiments F1-F4, wherein:
- part (b), part (c) and/or part (d) comprises applying a voltage bias, and
- part (b), part (c) and/or part (d) comprises adjusting the applied voltage bias.

F6. The method of embodiment F5, wherein part (b), part (c) and/or part (d) comprises decreasing the applied voltage bias after capturing the polymer.

F7. The method of embodiment F5 or embodiment F6, wherein part (d) comprises adjusting voltage bias, wherein the voltage bias is sufficient to:
electrophoretically drive at least a portion of the polymer through the first reader into the first well and overcome the voltage bias used to drive at least a portion of the polymer in the direction of the second reader in part (c), or
electrophoretically drive at least a portion of the polymer through the second reader into the second well and overcome the voltage bias used to drive at least a portion of the polymer in the direction of the first reader in part (b).

F8. The method of any one of embodiments F1-F7, comprising, after part (e) performing part (d') and part (e'):
- (d') electrophoretically driving at least a portion of the polymer through the first reader into the first well if the polymer was driven into the second well in part (d), or electrophoretically driving at least a portion of the polymer through the second reader into the second well if the polymer was driven into the first well in part (d); and
- (e') identifying monomeric units of the polymer based on a current signature of each of the monomeric units, translocation time and/or associated current noise level modulation as the polymer translocates through the first reader or the second reader in part (d'), thereby determining the sequence of the polymer.

F9. The method of embodiment F8, wherein part (d') comprises adjusting voltage bias, wherein
the voltage bias is sufficient to: electrophoretically drive at least a portion of the polymer through the first reader into the first well if the polymer was driven into the second reader in part (d), and overcome a voltage bias used to drive at least a portion of the polymer in the direction of the second reader, or electrophoretically drive at least a portion the polymer through the second reader into the second well if the polymer was driven into the first reader in part (d), and overcome a voltage bias used to drive at least a portion of the polymer in the direction of the first reader.

F10. The method of embodiment F8 or embodiment F9, wherein after part (d'):
- a portion of the polymer is in contact with the second reader after the polymer is electrophoretically driven through the first reader into the first well, or
- a portion of the polymer is in contact with the first reader after the polymer is electrophoretically driven through the second reader into the first well.

F11. The method of any one of embodiments F8-F10 comprising repeating parts (d) and (e) after performing parts (d') and (e').

F12. The method of embodiment F11 comprising repeating parts (d') and (e') after repeating parts (d) and (e).

F13. The method of any one of embodiments F8-F12, wherein parts (d) and (e) are performed alternately with parts (d') and (e') about 4 to about 10,000 times.

F14. The method of any one of embodiments F8-F13, wherein in part (d) and/or part (d') the entire polymer is electrophoretically driven through the first reader into the first well or through the second reader into the second well.

F15. The method of any one of embodiments F1-F14, wherein the first reader is linked to one or more magnetic particles, or the second reader is linked to one or more magnetic particles, or the first reader and the second reader each is independently linked to one or more magnetic particles.

F16. The method of any one of embodiments F1-F15, wherein:
the chip comprises a side,
each of the wells comprises a major length, and
the major length of each of the wells is disposed at an angle of about 5 degrees to about 85 degrees with respect to the side.

F17. The method of embodiment F16, wherein:
each of the wells comprises a minor width and a major width, and
the width of each of the wells narrows from the major width to the minor width as the distance between the wells decrease.

F18. The method of any one of embodiments F15-F17, comprising applying a magnetic field by a component configured to apply a magnetic field across the wells.

F19. The method of embodiment F18, wherein:
the first reader is linked independently to one or more magnetic particles and the magnetic field is of a strength sufficient to move via a magnetic force the first reader in the first seal after the field is applied; and/or
the second reader is linked independently to one or more magnetic particles and the magnetic field is of a strength sufficient to move via a magnetic force the second reader in the second seal after the field is applied.

F20. The method of any one of embodiments F17-F19, wherein the first reader and/or the second reader move via a magnetic force in the direction of a region of each of the wells defined by the minor width.

F21. The method of any one of embodiments F17-F20, wherein the device is a device of any one of embodiments D1-D29.

G1. A method of attaching a magnetic particle to a nanopore reader comprising:
providing a nanopore reader;
modifying a residue of the nanopore reader that is on the cis side of the reader when the reader is inserted into a seal to comprise an attachment site;
providing a bifunctional polymer linker having a first end and a second end, wherein a magnetic particle is attached to the first end of the polymer linker; and
conjugating the second end of the polymer linker to the attachment site on the cis side of the nanopore reader.

G2. The method of embodiment G1, wherein the magnetic particle is a nanoparticle.

G3. The method of embodiment G2, wherein the magnetic nanoparticle is about 5 nanometers to about 500 nanometers in diameter.

G4. The method of any one of embodiments G1-G3, wherein the linker has a length and the length is about 25-200 nm.

G5. The method of any one of embodiments G1-G4, wherein the linker is a maleimide-biotin linker.

G6. The method of any one of embodiments G1-G5, wherein the attachment site comprises a cysteine residue.

G7. The method of any one of embodiments G1-G4, wherein the linker is a double-stranded DNA linker.

G8. The method of any one of embodiments G1-G7, comprising isolating a nanopore reader conjugated to a single magnetic particle.

H1. A method for insertion of magnetic particle tagged nanopore readers into PLBs and migration of the magnetic particle tagged nanopore readers into a dual capture zone comprising:
providing a first and a second well with electrodes in each well, wherein the first well and the second well are on the same platform;
forming a first planar supported lipid bilayer over the first well and a second planar supported lipid bilayer over the second well;
applying high voltage bias to allow insertion of a particle-tagged nanopore reader into the first planar supported lipid bilayer;
applying high voltage bias to allow insertion of a particle-tagged nanopore reader into the second planar supported lipid bilayer; and
generating a high magnetic field gradient to move magnetic particle-tagged readers in the first planar supported lipid bilayer and the second planar supported lipid bilayer into a dual-capture zone.

H2. The method of embodiment H1, wherein the wells are photopatterned into SU-8 photoresist.

H3. The method of embodiment H1 or embodiment H2, wherein the electrodes are Ag/AgCl electrodes.

H4. The method of any one of embodiments H1 to H3, wherein the planar supported lipid bilayer is formed using a magnetic stir bar or lipid painting method.

H5. The method of any one of embodiments H1 to H4, wherein the high voltage bias is 100-300 mV.

H6. The method of any one of embodiments H1 to H5, wherein the nanopore reader type inserted into the first planar supported lipid bilayer is different from the nanopore reader type inserted into the second planar supported lipid bilayer H7. The method of any one of embodiments H1 to H6, wherein the particle-tagged nanopore reader inserted into the first planar supported lipid bilayer is αHL.

H7.1. The method of any one of embodiments H1 to H6, wherein the particle-tagged nanopore reader inserted into the second planar supported lipid bilayer is MspA.

H8. The method of any one of embodiments H1 to H7.1, wherein the platform is a chip.

I1. A method for sequencing using dual biological nanopore readers comprising:
providing two adjacent biological nanopore readers tagged with magnetic particles;
positioning the magnetic particle-tagged readers into proximity by an external magnetic field;
capturing one end of a polymer by the first nanopore reader by providing high positive voltage bias to the first nanopore reader;
reducing the voltage bias on the first nanopore reader and capturing the other end of the polymer by the second nanopore reader by providing high positive voltage bias to the second nanopore reader;
applying a small voltage bias between the first nanopore reader and the second nanopore reader to initiate dual pore sequencing; and
reversing the voltage bias between the first nanopore reader and the second nanopore reader to initiate reverse translocation and sequencing.

I2. The method of embodiment I1, wherein the polymer is a single-stranded molecule.

I3. The method of embodiment I2, wherein the polymer is single-stranded DNA or single-stranded RNA.

I4. The method of embodiment I1, wherein the polymer is double-stranded DNA or double-stranded RNA.

I5. The method of embodiment I1, wherein the polymer is a protein or a peptide.

I6. The method of embodiment I1, wherein reversing the voltage bias between the first nanopore reader and the second nanopore reader is repeated to sequence the polymer multiple times.

J1. A method for sequencing a polymer comprising:
providing adjacent nanopore readers;
contacting the adjacent nanopore readers with a polymer; and
capturing the polymer with the adjacent nanopore readers; and
controlling the voltage bias applied between the two nanopore readers to floss the polymer between the two readers and to allow multipass sequencing.

J2. The device of embodiment J1, wherein the polymer is a nucleic acid.

J3. The device of embodiment J2, wherein the nucleic acid is single-stranded RNA or single-stranded DNA.

J4. The device of embodiment J2, wherein the nucleic acid is double-stranded RNA or double-stranded DNA.

J5. The device of embodiment J1, wherein the polymer is a protein or a peptide.

K1. A nanopore reader tethered to one or more magnetic particles.

K2. The nanopore reader of embodiment K1, wherein the particles are nanoparticles.

K3. The nanopore reader of embodiment K1 or embodiment K2, wherein the nanopore reader is tethered to a magnetic particle via a linker.

K4. The nanopore reader of embodiment K3, wherein the linker has a length and the length is about 25-200 nm.

K5. The nanopore reader of embodiment K3 or embodiment K4, wherein the linker is a maleimide-biotin linker.

K6. The nanopore reader of embodiment K3 or embodiment K4, wherein the linker is engineered to comprise a cysteine-reactive functional group.

K7. The nanopore reader of embodiment K3 or embodiment K4, wherein the linker is a double-stranded DNA linker.

K8. The nanopore reader of any one of embodiments K1-K7, wherein the nanopore reader is modified to comprise cysteine.

L1. A method of sequencing comprising;
providing two adjacent biological nanopore readers;
contacting a polymer comprising monomeric units with the two adjacent biological nanopore readers; and
identifying monomeric units of the polymer as the polymer translocates through one or both adjacent biological nanopore readers.

L2. The method of embodiment L1, wherein the polymer is a nucleic acid.

L3. The method of embodiment L2, wherein the nucleic acid is single-stranded RNA or single-stranded DNA.

L4. The method of embodiment L2, wherein the nucleic acid is double-stranded RNA or double-stranded DNA.

L5. The method of embodiment L1, wherein the polymer is a protein or a peptide.

L6. The method of any one of embodiments L1-L5, wherein each reader independently is chosen from a biological nanopore, an ion channel, a transmembrane protein or an engineered DNA or peptide nanopore.

L7. The method of any one of embodiments L1-L5, wherein each reader independently is chosen from alpha-hemolysin (αHL), aerolysin, Mycobacterium smegmatis porin A (MspA), Escherichia coli CsgG, cytolysin A (ClyA), or outer membrane protein F (OmpF).

L7.1. The method of embodiment L7, wherein one reader is alpha-hemolysin (αHL) and one reader is Mycobacterium smegmatis porin A (MspA).

L8. The method of any one of embodiments L1-L7.1, wherein, wherein the adjacent biological nanopore readers are the same.

L9. The method of any one of embodiments L1-L7, wherein, wherein the adjacent biological nanopore readers are different.

M1. A method of sequencing comprising utilizing a sequencing chip and a magnetic field.

M2. The method of embodiment M1, wherein the sequencing chip comprises:
a first well disposed adjacent to a second well on the chip,
a first seal over the first well and a second seal over the second well, and a first reader in the first seal and a second reader in the second seal, wherein the first reader and the second reader each is a nanopore reader.

M3. The method of embodiment M2, wherein the first reader and the second reader are each tethered to one or more magnetic particles.

M4. The method of embodiment M3, wherein the magnetic field is applied across the wells to move the first and the second reader each tethered to one or more magnetic particles.

M5. The method of any one of embodiments M2-M4, wherein each seal comprises a membrane capable of retaining a reader.

M6. The method of any one of embodiments M2-M5, wherein each seal independently comprises a planar lipid bilayer, surfactant bilayer, deblock copolymer bilayer or triblock copolymer monolayer.

M7. The method of any one of embodiments M2-M6, wherein each reader independently is chosen from a biological nanopore, an ion channel, a transmembrane protein or an engineered DNA or peptide nanopore.

M8. The method of any one of embodiments M2-M6, wherein each reader independently is chosen from alpha-hemolysin (αHL), aerolysin, Mycobacterium smegmatis porin A (MspA), Escherichia coli CsgG, cytolysin A (ClyA), or outer membrane protein F (OmpF).

M9. The method of any one of embodiments M1-M8, wherein the magnetic field is an external magnetic field.

N1. A chip comprising dual wells.

N2. The chip of embodiment N1, wherein the wells are adjacent to each other.

N3. The chip of embodiment N1 or N2, wherein the two adjacent wells are separated by a distance.

N4. The chip of embodiment N3, wherein the distance is about 10 nm to about 1000 nm.

N5. The chip of any one of embodiments N1-N4, wherein each of the wells comprises an opening aperture, a bottom and an electrode disposed at the bottom.

N6. The chip of any one of embodiments N1-N5, wherein a separate seal is over the opening aperture of each of the wells.

The entirety of each patent, patent application, publication and document referenced herein is incorporated by reference. Citation of patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness. The technology has been described with reference to specific implementations. The terms and expressions that have been utilized herein to describe the technology are descriptive and not necessarily limiting. Certain modifications made to the disclosed implementations can be considered within the scope of the technology. Certain aspects of the disclosed implementations suitably may be practiced in the presence or absence of certain elements not specifically disclosed herein.

Each of the terms "comprising," "consisting essentially of," and "consisting of" may be replaced with either of the other two terms. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%; e.g., a weight of "about 100 grams" can include a weight between 90 grams and 110 grams). Use of the term "about" at the beginning of a listing of values modifies each of the values (e.g., "about 1, 2 and 3" refers to "about 1, about 2 and about 3"). When a listing of values is described the listing includes all intermediate values and all fractional values thereof (e.g., the listing of values "80%, 85% or 90%" includes the intermediate value 86% and the fractional value 86.4%). When a listing of values is followed by the term "or more," the term "or more" applies to each of the values listed (e.g., the listing of "80%, 90%, 95%, or more" or "80%, 90%, 95% or more" or "80%, 90%, or 95% or more" refers to "80% or more, 90% or more, or 95% or more"). When a listing of values is described, the listing includes all ranges between any two of the values listed (e.g., the listing of "80%, 90% or 95%" includes ranges of "80% to 90%," "80% to 95%" and "90% to 95%").

Certain implementations of the technology are set forth in the claims that follow.

What is claimed is:

1. A device, comprising:
a chip comprising two adjacent wells separated by a distance, each of the wells comprising an opening aperture, a bottom and an electrode disposed at the bottom;
a separate seal over the opening aperture of each of the wells;
a nanopore reader in each seal, wherein each reader independently is tethered to one or more magnetic particles;
a first component configured to apply a magnetic field across the wells to magnetically position each reader in each separate seal in each of the two adjacent wells at a distance of about 10 nanometers to 5 micrometers from one other; and
a second component configured to detect an interaction between each reader and a molecule that can be introduced to the device and contacted by a reader.

2. The device of claim 1, wherein the magnetic particles comprise magnetic nanoparticles having an average diameter of between about 5 nanometers to about 500 nanometers.

3. The device of claim 1, wherein the second component comprises a controllable voltage source configured to quantify direct current (DC) and/or alternating current (AC).

4. The device of claim 3, wherein the second component is configured to quantify a change in conductance of the reader, thereby permitting detection of an interaction between a molecule and the reader.

5. The device of claim 1, wherein each seal comprises a membrane capable of retaining the reader.

6. The device of claim 5, wherein each seal independently comprises a planar lipid bilayer, a surfactant bilayer, a deblock copolymer bilayer or a triblock copolymer monolayer.

7. The device of claim 1, wherein each reader independently is chosen from a biological nanopore, an ion channel, a transmembrane protein or an engineered DNA or peptide nanopore.

8. The device of claim 1, wherein each reader independently is chosen from alpha-hemolysin (aHL), aerolysin, Mycobacterium smegmatis porin A (MspA), Escherichia coli CsgG, cytolysin A (ClyA), or outer membrane protein F (OmpF).

9. The device of claim 8, wherein one reader is alpha-hemolysin (aHL) and one reader is Mycobacterium smegmatis porin A (MspA).

10. The device of claim 1, wherein the reader in one separate seal is different than the reader in the other separate seal.

11. The device of claim 1, wherein the distance between the closest points between the opening apertures of the wells is about 1 nanometer to about 50 micrometers.

12. The device of claim 1, wherein:
each of the wells comprises a major length and a virtual major axis parallel to the major length, and
the virtual major axis of one of the wells is disposed at an angle of about 5 degrees to about 120 degrees with respect to the virtual major axis of the other well.

13. The device of claim 1, wherein:
each of the wells comprises a minor width and a major width, and
the width of each of the wells narrows from the major width to the minor width as the distance between the wells decreases.

14. The device of claim 13, wherein:
the first component is configured to move, after application of a magnetic force, each reader in the direction of a region of each of the wells defined by the minor width.

15. The device of claim 1, wherein the opening aperture of each of the wells independently comprises a perimeter shape defined by a teardrop, curvilinear triangle, crescent, circle, oval, ellipse, parabola, hyperbola, annulus, lens, circular segment, circular sector, heart, trefoil, quatrefoil, pill, polygon, quadrilateral, trapezoid, square or rectangle.

16. The device of claim 1, wherein the molecule is a polymer, comprising monomers, that can be translocated by each reader and the second component is configured to detect an interaction between a reader and a monomer of the polymer.

17. The device of claim 1, wherein the first component comprises one or more of:
(a) an external magnet; a permanent magnet; a permanent rare earth magnet; a magnetic tip; a magnetic tweezer; a magnetic nanostructure; a magnetic strip; a magnetic probe; a magnetic coil; an electromagnetic coil; a wire coil electromagnet; and/or a thin film microstructure magnetic circuit; and
(b) a magnetic microstructure made of a material comprising a ferromagnetic, a paramagnetic and/or a super paramagnetic material.

18. The device of claim 3, wherein the second component comprises an amplifier.

19. The device of claim 18, wherein the amplifier comprises a DC bias.

20. The device of claim 19, wherein the DC bias is controlled by a field-programmable gate array (FPGA).

21. The device of claim 18, wherein the second component comprises two amplifiers.

* * * * *